United States Patent
Mamluk et al.

(10) Patent No.: US 12,251,418 B2
(45) Date of Patent: *Mar. 18, 2025

(54) METHOD OF TREATING DISEASES

(71) Applicant: Amryt Endo, Inc., Boston, MA (US)

(72) Inventors: Roni Mamluk, Mazkeret Batya (IL); Sam L. Teichman, Oakland, CA (US)

(73) Assignee: Amryt Endo, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/599,127

(22) Filed: Mar. 7, 2024

(65) Prior Publication Data
US 2024/0245749 A1 Jul. 25, 2024

Related U.S. Application Data

(63) Continuation of application No. 18/514,644, filed on Nov. 20, 2023, which is a continuation of application No. 17/721,725, filed on Apr. 15, 2022, now Pat. No. 11,857,595, which is a continuation of application No. 17/094,238, filed on Nov. 10, 2020, now Pat. No. 11,338,011, which is a continuation of application No. 16/881,348, filed on May 22, 2020, now Pat. No. 11,052,126, which is a continuation of application No. 16/233,749, filed on Dec. 27, 2018, now Pat. No.
(Continued)

(51) Int. Cl.
| | |
|---|---|
| *A61K 38/08* | (2019.01) |
| *A61K 9/00* | (2006.01) |
| *A61K 9/48* | (2006.01) |
| *A61K 38/31* | (2006.01) |
| *A61P 5/06* | (2006.01) |

(52) U.S. Cl.
CPC ............ *A61K 38/08* (2013.01); *A61K 9/0053* (2013.01); *A61K 9/4858* (2013.01); *A61K 38/31* (2013.01); *A61P 5/06* (2018.01)

(58) Field of Classification Search
CPC .... A61K 38/08; A61K 9/0053; A61K 9/4858; A61K 38/31; A61P 5/06
See application file for complete search history.

(56) References Cited

U.S. PATENT DOCUMENTS

| | | |
|---|---|---|
| 3,869,549 A | 3/1975 | Geller |
| 4,156,719 A | 5/1979 | Sezaki et al. |
| (Continued) | | |

FOREIGN PATENT DOCUMENTS

| | | |
|---|---|---|
| CA | 2003340 A1 | 5/1990 |
| CA | 2044511 A1 | 12/1991 |
| (Continued) | | |

OTHER PUBLICATIONS

Ho et al. (Anals of Internal Medicine 1990; 112(3):173-181) (Year: 1990).*
(Continued)

*Primary Examiner* — Ernst V Arnold
(74) *Attorney, Agent, or Firm* — COOLEY LLP

(57) ABSTRACT

Methods of treating acromegaly in a subject are described herein. Exemplary methods include orally administering to the subject at least once daily at least one dosage form comprising octreotide, wherein the octreotide in each dosage form is 20 mg, and wherein the administering occurs at least 1 hour before a meal or at least 2 hours after a meal.

21 Claims, 4 Drawing Sheets

Related U.S. Application Data 10,695,397, which is a continuation of application No. 15/014,634, filed on Feb. 3, 2016, now Pat. No. 10,238,709.

(60) Provisional application No. 62/136,012, filed on Mar. 20, 2015, provisional application No. 62/111,369, filed on Feb. 3, 2015.

(56) References Cited

U.S. PATENT DOCUMENTS

| | | | |
|---|---|---|---|
| 4,234,437 A | 11/1980 | Friberg et al. | |
| 4,338,306 A | 7/1982 | Kitao et al. | |
| 4,411,890 A | 10/1983 | Momany | |
| 4,485,033 A | 11/1984 | Kitao et al. | |
| 4,489,097 A | 12/1984 | Stone | |
| 4,508,828 A | 4/1985 | Lindall et al. | |
| 4,544,500 A | 10/1985 | Bittle et al. | |
| 4,572,915 A | 2/1986 | Crooks | |
| 4,589,881 A | 5/1986 | Pierschbacher et al. | |
| 4,650,665 A | 3/1987 | Kronenthal et al. | |
| 4,650,787 A | 3/1987 | Schally et al. | |
| 4,839,344 A | 6/1989 | Bowers et al. | |
| 4,871,777 A | 10/1989 | Breitzke | |
| 4,895,726 A | 1/1990 | Curtet et al. | |
| 4,985,404 A | 1/1991 | Mitchell | |
| 5,200,192 A | 4/1993 | Wimmer | |
| 5,206,219 A | 4/1993 | Desai | |
| 5,246,716 A | 9/1993 | Sedun et al. | |
| 5,254,331 A | 10/1993 | Mausner | |
| 5,288,492 A | 2/1994 | Morris | |
| 5,318,781 A | 6/1994 | Shah et al. | |
| 5,354,883 A | 10/1994 | Isak et al. | |
| 5,393,738 A | 2/1995 | Vonderscher et al. | |
| 5,443,842 A | 8/1995 | Seghizzi et al. | |
| 5,462,726 A | 10/1995 | Lodge | |
| 5,491,171 A | 2/1996 | Nishimura et al. | |
| 5,506,203 A | 4/1996 | Backstrom et al. | |
| 5,561,115 A | 10/1996 | Tenold | |
| 5,656,289 A | 8/1997 | Cho et al. | |
| 5,658,878 A | 8/1997 | Backstrom et al. | |
| 5,665,384 A | 9/1997 | Courteille et al. | |
| 5,665,711 A | 9/1997 | Sakai et al. | |
| 5,686,488 A | 11/1997 | Gamache et al. | |
| 5,714,477 A | 2/1998 | Einarsson | |
| 5,726,154 A | 3/1998 | Baudys et al. | |
| 5,738,871 A | 4/1998 | Story | |
| 5,760,096 A | 6/1998 | Thornfeldt et al. | |
| 5,804,573 A | 9/1998 | Silver | |
| 5,827,534 A | 10/1998 | Fasano | |
| 5,840,685 A | 11/1998 | Fujii et al. | |
| 5,853,748 A | 12/1998 | New | |
| 5,858,401 A | 1/1999 | Bhalani et al. | |
| 5,859,048 A | 1/1999 | Oohashi et al. | |
| 5,929,030 A | 7/1999 | Hamied et al. | |
| 5,942,237 A | 8/1999 | Gizurarson et al. | |
| 6,013,657 A | 1/2000 | Lavon et al. | |
| 6,096,338 A | 8/2000 | Lacy et al. | |
| 6,114,319 A | 9/2000 | Kimura et al. | |
| 6,120,801 A | 9/2000 | Parekh et al. | |
| 6,136,336 A | 10/2000 | Tanaka et al. | |
| 6,150,333 A | 11/2000 | Moreau | |
| 6,190,702 B1 | 2/2001 | Takada et al. | |
| 6,193,986 B1 | 2/2001 | Sakurada | |
| 6,200,602 B1 | 3/2001 | Watts et al. | |
| 6,214,380 B1 | 4/2001 | Parekh et al. | |
| 6,214,792 B1 | 4/2001 | Simon | |
| 6,255,502 B1 | 7/2001 | Penkler et al. | |
| 6,284,223 B1 | 9/2001 | Luiken | |
| 6,322,550 B2 | 11/2001 | Iga et al. | |
| 6,326,026 B1 | 12/2001 | Parekh et al. | |
| 6,326,360 B1 | 12/2001 | Kanazawa et al. | |
| 6,333,046 B1 | 12/2001 | Sakai et al. | |
| 6,365,596 B1 | 4/2002 | Valenti | |
| 6,368,622 B2 | 4/2002 | Chen et al. | |
| 6,383,527 B1 | 5/2002 | Artman et al. | |
| 6,395,708 B1 | 5/2002 | Miller et al. | |
| 6,419,949 B1 | 7/2002 | Gasco | |
| 6,428,813 B1 | 8/2002 | Akiyama et al. | |
| 6,632,443 B2 | 10/2003 | Borowy-Borowski et al. | |
| 6,664,234 B1 | 12/2003 | Heintz et al. | |
| 6,696,413 B2 | 2/2004 | Fischer et al. | |
| 6,710,195 B2 | 3/2004 | Joshi-Hangal et al. | |
| 6,720,002 B2 | 4/2004 | Lin et al. | |
| 6,770,292 B2 | 8/2004 | Guinez et al. | |
| 6,835,396 B2 | 12/2004 | Brynjelsen et al. | |
| 6,890,961 B2 | 5/2005 | Li et al. | |
| 7,141,547 B2 | 11/2006 | Rosen et al. | |
| 7,217,431 B2 | 5/2007 | Holm et al. | |
| 7,288,520 B2 | 10/2007 | Chang et al. | |
| 7,411,039 B2 | 8/2008 | Thim et al. | |
| 7,759,312 B2 | 7/2010 | Kuzma et al. | |
| 8,133,863 B2 | 3/2012 | Maggio | |
| 8,241,670 B2 | 8/2012 | Ben-Sasson | |
| 8,329,198 B2 | 12/2012 | Salama et al. | |
| 8,535,695 B2 * | 9/2013 | Salama | A61K 38/29 424/408 |
| 8,822,637 B2 | 9/2014 | Albert et al. | |
| 8,883,203 B2 | 11/2014 | Leonard | |
| 9,265,812 B2 | 2/2016 | Mamluk et al. | |
| 9,566,246 B2 | 2/2017 | Mamluk et al. | |
| 10,238,709 B2 * | 3/2019 | Mamluk | A61K 38/08 |
| 10,682,387 B2 | 6/2020 | Haviv | |
| 10,695,397 B2 * | 6/2020 | Mamluk | A61P 5/06 |
| 11,052,126 B2 * | 7/2021 | Mamluk | A61K 9/0053 |
| 11,141,457 B1 | 10/2021 | Haviv et al. | |
| 11,338,011 B2 * | 5/2022 | Mamluk | A61K 9/0053 |
| 11,400,159 B2 | 8/2022 | Mamluk et al. | |
| 11,510,963 B1 * | 11/2022 | Mamluk | A61K 38/08 |
| 11,857,595 B2 * | 1/2024 | Mamluk | A61K 38/31 |
| 11,890,316 B2 | 2/2024 | Haviv et al. | |
| 11,969,471 B2 | 4/2024 | Mamluk et al. | |
| 11,986,529 B2 | 5/2024 | Mamluk et al. | |
| 2001/0055569 A1 | 12/2001 | Davis et al. | |
| 2002/0091623 A1 | 7/2002 | Daniels | |
| 2002/0151495 A1 | 10/2002 | Wolfe et al. | |
| 2002/0188148 A1 | 12/2002 | O'Lenick, Jr. et al. | |
| 2003/0091623 A1 | 5/2003 | Cumming et al. | |
| 2003/0095928 A1 | 5/2003 | McGurk et al. | |
| 2003/0108610 A1 | 6/2003 | Flore et al. | |
| 2003/0125528 A1 | 7/2003 | Hay et al. | |
| 2003/0153614 A1 | 8/2003 | Joshi-Hangal et al. | |
| 2003/0162695 A1 | 8/2003 | Schatzberg et al. | |
| 2003/0166508 A1 | 9/2003 | Zhang | |
| 2003/0176379 A1 | 9/2003 | Raoof et al. | |
| 2004/0009231 A1 | 1/2004 | Jackson et al. | |
| 2004/0097419 A1 | 5/2004 | Petersen et al. | |
| 2004/0147599 A1 | 7/2004 | Gagnon et al. | |
| 2004/0167205 A1 | 8/2004 | Joshi-Hangal et al. | |
| 2004/0185170 A1 | 9/2004 | Chungi et al. | |
| 2004/0248901 A1 | 12/2004 | Lee et al. | |
| 2004/0253723 A1 | 12/2004 | Tachas et al. | |
| 2005/0004002 A1 | 1/2005 | Desai et al. | |
| 2005/0112191 A1 | 5/2005 | Lipari et al. | |
| 2005/0142225 A1 | 6/2005 | Kysilka et al. | |
| 2005/0186277 A1 | 8/2005 | Gale et al. | |
| 2005/0209441 A1 | 9/2005 | Lile | |
| 2005/0232981 A1 | 10/2005 | Ben-Sasson | |
| 2005/0256097 A1 | 11/2005 | Zhong et al. | |
| 2005/0287203 A1 | 12/2005 | Nijs De et al. | |
| 2006/0002989 A1 | 1/2006 | Ahmed et al. | |
| 2006/0014712 A1 | 1/2006 | Neuman | |
| 2006/0052404 A1 | 3/2006 | Rudolph et al. | |
| 2006/0057185 A1 | 3/2006 | Akimoto et al. | |
| 2006/0069055 A1 | 3/2006 | Dajee et al. | |
| 2006/0078618 A1 | 4/2006 | Constantinides et al. | |
| 2006/0128800 A1 | 6/2006 | Penney et al. | |
| 2006/0165809 A1 | 7/2006 | Guimberteau et al. | |
| 2006/0188566 A1 | 8/2006 | Liversidge et al. | |
| 2006/0189662 A1 | 8/2006 | Goto et al. | |
| 2006/0204540 A1 | 9/2006 | Kuzma et al. | |
| 2006/0275253 A1 | 12/2006 | Ushida et al. | |
| 2007/0004668 A1 | 1/2007 | Raoof et al. | |
| 2007/0015694 A1 | 1/2007 | Chang et al. | |

(56) References Cited

U.S. PATENT DOCUMENTS

| | | |
|---|---|---|
| 2007/0021325 A1 | 1/2007 | Byun et al. |
| 2007/0066512 A1 | 3/2007 | Verhelle et al. |
| 2007/0104741 A1 | 5/2007 | Murty et al. |
| 2007/0134319 A1 | 6/2007 | Zannou et al. |
| 2007/0148228 A1 | 6/2007 | Cumming et al. |
| 2007/0185194 A1 | 8/2007 | Mehta et al. |
| 2007/0190139 A1 | 8/2007 | Zerbe et al. |
| 2007/0196464 A1 | 8/2007 | Cumming et al. |
| 2007/0207214 A1 | 9/2007 | Castan et al. |
| 2007/0219131 A1 | 9/2007 | Ben-Sasson |
| 2007/0224142 A1 | 9/2007 | Swaile et al. |
| 2007/0237832 A1 | 10/2007 | Sackler et al. |
| 2007/0237833 A1 | 10/2007 | Sackler et al. |
| 2007/0238707 A1 | 10/2007 | Leonard |
| 2007/0248549 A1 | 10/2007 | Kuhrts |
| 2007/0248668 A1 | 10/2007 | Michaelis et al. |
| 2007/0254954 A1 | 11/2007 | Sakakibara et al. |
| 2007/0259098 A1 | 11/2007 | Gulian et al. |
| 2007/0292512 A1 | 12/2007 | Leonard et al. |
| 2008/0139392 A1 | 6/2008 | Acosta-Zara et al. |
| 2008/0255029 A1 | 10/2008 | Marks et al. |
| 2008/0275001 A1 | 11/2008 | Cumming et al. |
| 2009/0220611 A1 | 9/2009 | Dargelas et al. |
| 2009/0246172 A1 | 10/2009 | Rothermel et al. |
| 2009/0280169 A1 | 11/2009 | Leonard |
| 2010/0028421 A1 | 2/2010 | Cumming et al. |
| 2010/0105627 A1 | 4/2010 | Salama et al. |
| 2010/0151033 A1 | 6/2010 | Ahlheim et al. |
| 2010/0285143 A1 | 11/2010 | Khedkar et al. |
| 2011/0142800 A1 | 6/2011 | Kidron et al. |
| 2011/0257095 A1 | 10/2011 | Salama et al. |
| 2012/0009229 A1 | 1/2012 | Salama et al. |
| 2012/0093886 A1 | 4/2012 | Salama et al. |
| 2014/0188042 A1 | 7/2014 | Browning |
| 2015/0031631 A1 | 1/2015 | Mamluk et al. |
| 2015/0141338 A1 | 5/2015 | Fujiki et al. |
| 2015/0141349 A1 | 5/2015 | Davis et al. |
| 2015/0258179 A1 | 9/2015 | LaRusso et al. |
| 2015/0283147 A1 | 10/2015 | Proia et al. |
| 2016/0158159 A1 | 6/2016 | Mamluk et al. |
| 2016/0193285 A1 | 7/2016 | Haviv |
| 2016/0220628 A1 | 8/2016 | Mamluk |
| 2017/0112938 A1 | 4/2017 | Mamluk et al. |
| 2017/0266183 A1 | 9/2017 | Koziol |
| 2019/0038758 A1 | 2/2019 | Mamluk et al. |
| 2019/0091285 A1 | 3/2019 | Haviv |
| 2019/0298792 A1 | 10/2019 | Mamluk et al. |
| 2020/0390847 A1 | 12/2020 | Mamluk et al. |
| 2020/0397906 A1 | 12/2020 | Mamluk et al. |
| 2021/0052691 A1 | 2/2021 | Mamluk et al. |
| 2021/0077569 A1 | 3/2021 | Haviv |
| 2021/0187079 A1 | 6/2021 | Mamluk et al. |
| 2022/0202911 A1 | 6/2022 | Teichman et al. |
| 2022/0233630 A1 | 7/2022 | Mamluk et al. |
| 2022/0233633 A1 | 7/2022 | Haviv et al. |
| 2022/0339240 A1 | 10/2022 | Haviv |
| 2022/0370621 A1 | 11/2022 | Mamluk et al. |
| 2022/0370622 A1 | 11/2022 | Mamluk et al. |
| 2022/0378867 A1 | 12/2022 | Mamluk et al. |
| 2023/0173034 A1 | 6/2023 | Mamluk et al. |
| 2023/0201302 A1 | 6/2023 | Asi et al. |
| 2024/0016899 A1 | 1/2024 | Mamluk et al. |
| 2024/0041973 A1 | 2/2024 | Haviv et al. |
| 2024/0050533 A1 | 2/2024 | Teichman et al. |
| 2024/0082343 A1 | 3/2024 | Mamluk et al. |
| 2024/0123024 A1 | 4/2024 | Haviv et al. |
| 2024/0245748 A1 | 7/2024 | Mamluk et al. |

FOREIGN PATENT DOCUMENTS

| | | |
|---|---|---|
| CA | 2069760 A1 | 3/1992 |
| CA | 2363123 A1 | 8/2000 |
| CA | 2563533 A1 | 9/2006 |
| CA | 2655273 A1 | 12/2007 |
| CN | 1960746 A | 5/2007 |
| CN | 101084016 A | 12/2007 |
| EP | 0204480 A3 | 2/1989 |
| EP | 0366277 A2 | 5/1990 |
| EP | 0370481 A2 | 5/1990 |
| EP | 0480189 A1 | 4/1992 |
| EP | 0554767 A1 | 8/1993 |
| EP | 1154761 A1 | 11/2001 |
| EP | 1424077 A1 | 6/2004 |
| EP | 2123255 A1 | 11/2009 |
| EP | 2343982 A2 | 7/2011 |
| IE | 63119 B1 | 3/1995 |
| IL | 252689 A | 9/2021 |
| JP | 2007528388 A | 10/2007 |
| JP | 2010510206 A | 4/2010 |
| JP | 2011503160 A | 1/2011 |
| JP | 2011113487 A | 6/2011 |
| WO | WO-8707149 A1 | 12/1987 |
| WO | WO-9317037 A1 | 9/1993 |
| WO | WO-9631213 A1 | 10/1996 |
| WO | WO-9705903 A2 | 2/1997 |
| WO | WO-0047203 A1 | 8/2000 |
| WO | WO-0050012 A1 | 8/2000 |
| WO | WO-0074736 A1 | 12/2000 |
| WO | WO-0101960 A1 | 1/2001 |
| WO | WO-03004001 A1 | 1/2003 |
| WO | WO-03013589 A1 | 2/2003 |
| WO | WO-03037345 A1 | 5/2003 |
| WO | WO-03060071 A2 | 7/2003 |
| WO | WO-2004087052 A2 | 10/2004 |
| WO | WO-2005000012 A1 | 1/2005 |
| WO | WO-2005041901 A2 | 5/2005 |
| WO | WO-2005046642 A1 | 5/2005 |
| WO | WO-2005087194 A1 | 9/2005 |
| WO | WO-2005094785 A2 | 10/2005 |
| WO | WO-2005115333 A2 | 12/2005 |
| WO | WO-2006013369 A2 | 2/2006 |
| WO | WO-2006097793 A2 | 9/2006 |
| WO | WO-2006123360 A2 | 11/2006 |
| WO | WO-2006127214 A1 | 11/2006 |
| WO | WO-2007071395 A1 | 6/2007 |
| WO | WO-2007095091 A2 | 8/2007 |
| WO | WO-2008066279 A1 | 6/2008 |
| WO | WO-2008092084 A2 | 7/2008 |
| WO | WO-2009102443 A2 | 8/2009 |
| WO | WO-2010032140 A2 | 3/2010 |
| WO | WO-2011032140 A1 | 3/2011 |
| WO | WO-2011112576 A1 | 9/2011 |
| WO | WO-2014049515 A1 | 4/2014 |
| WO | WO-2016094662 A1 | 6/2016 |
| WO | WO-2016126830 A1 | 8/2016 |
| WO | WO-2017127710 A1 | 7/2017 |
| WO | WO-2023164614 A1 | 8/2023 |

OTHER PUBLICATIONS

Sandostatin LAR® Depot ([online] retrieved from: https://www.accessdata.fda.gov/drugsatfda_docs/label/2006/021008s018s019lbl.pdf; 1998: 17 pages) (Year: 1998).*

Adelman et al. "Acromegaly: the disease, its impact on patients, and managing the burden of long-term treatment" International Journal of General Medicine (2013) vol. 6, pp. 31-38.

Aliautdin RN., et al., "[Drug delivery to the brain with nanoparticles]", [Article in Russian] Eksp Klin Farmakol. Mar.-Apr. 2003; 66(2): 65-8, (Abstract), 1 page.

Ansel, H.C. et al., Pharmaceutical Dosage Forms and Drug Delivery Systems, 7th Ed. Lippincott Williams & Wilkins, 1999; pp. 48. 2 pages.

Armstrong, "Cellular Mechanisms of Ion Transport in The Small Intestine", Physiology of the Gastrointestinal Tract, Chapter 45, 2nd Ed., Johnson, ed., Raven Press, New York, 2: 1251-1265, 1987.

Aungst et al., "Enhancement of intestinal absorption of peptides and non-peptides" J. of Controlled Release, vol. 41, pp. 19-31 (1996).

Azziz et al., "Androgen excess disorders in women: polycystic ovary syndrome and other disorders second edition," Humana Press Inc., 2006, pp. 1-459.

Bernkop-Schnürch, "The use of inhibitory agents to overcome the enzymatic barrier to perorally administered therapeutic peptides and proteins." J. Control. Release, 52: 1-16, 1998.

(56) References Cited

OTHER PUBLICATIONS

Besson et al. "Sclerotherapy With or Without Octreotide for Acute Variceal Bleeding" The New England Journal of Medicine (1995) vol. 333, No. 9, pp. 555-560.
Biousse et al. "Update on the pathophysiology and management of idiopathic intracranial hypertension", J Neurol Neurosurg Psychiatry (2012) vol. 83, pp. 488-494.
Caron, P.H., et al., "Efficacy of the New Long-acting Formulation of Lanreotide (Lanreotide Autogel) in the Management of Acromegaly," The Journal of Clinical Endocrinology & Metabolism, Jan. 1, 2002, vol. 87(1), pp. 99-104.
Chanson et al. "Comparison of octreotide acetate LAR and lanreotide SR in patients with acromegaly" Clinical Endocrinology (2000) vol. 53, pp. 577-586.
Citi, "Protein kinase inhibitors prevent junction dissociation induced by low extracellular calcium in MDCK epithelial cells." J Cell Biol, 117(1): 169-178 (1992).
Constantinides, et. al., "Formulation and intestinal absorption enhancement evaluation of water-in-oil micro emulsions incorporating medium-chain glycerides." Pharm. Res., 11(10): 1385-1390 (1994).
Corley, et al., "Octreotide for acute esophageal variceal bleeding: A meta-analysis", Gastroenterology, 2001; 120: 946-954 (2001 ).
Costa et al. "Octreotide—A Review of its Use in Treating Neuroendocrine Tumours" European Oncology Haematology, (2013) vol. 9, No. 2, pp. 105-109.
"Dad found drug for sick daughter using internet research", The Sentinel, Jul. 22, 2010. 2 pages.
Deftereos et al. "Treatment of idiopathic intracranial hypertension: Is there a place for octreotide?" Cephalalgia (2011) vol. 31, No. 16, pp. 1679-1680.
Delie, "Evaluation of nano- and microparticle uptake by the gastrointestinal tract." Adv. Drug Del. Rev., 34(1): 221-233 (1998).
Dorkoosh et al. "Peroral Absorption of Octreotide in Pigs Formulated in Delivery Systems on the Basis of Superporous Hydrogel Polymers", Pharmaceutical Research (2002) vol. 19, No. 10 pp. 1532-1536.
Drewe et al. "Enteral absorption of octreotide: absorption enhancement by polyoxyethylene-24-cholesterol ether", Br. J. Pharmacol. (1993) vol. 108, pp. 298-303.
Duarte et al. "Clomiphene citrate for treatment of acromegaly not controlled by conventional therapies", Journal of Clinical Endocrinology Metabolism (2015) 100(5): 1863-1869; 8 pages.
Duarte et al. "Impact of clomiphene citrate on IGF-1 and testosterone levels in acromegalic patients non controlled by conventional therapy", Endocrine Reviews, Endocrine Society's 96th Annual Meeting and Expo, Jun. 21-24, 2014, Chicago, http://press.endocrine.org/doi/abs/10.1210/endo.meetings.2014.NP.28.MON.0732, 2 pages.
Edmunds et al., "Effect of octreotide on gastric and small bowel motility in patients with gastroparesis," Aliment Pharmacol. Ther. (1998) vol. 12, No. 2, pp. 167-174.
European Office Action dated Dec. 16, 2011 for application No. 05 857 653.9-1219. 6 pages.
Extended European Search Report for Application No. 17742029.6, dated Sep. 10, 2019, 6 pages.
Farthing, M.J.G., "Octreotide in dumping and short bowel syndromes," Digestion (1993) vol. 54, Suppl. 1, pp. 47-52 (Abstract), 2 pages.
Farthing. "Octreotide in the treatment of refractory diarrhoea and intestinal fistulae," Gut 1994, Supplement 3, S5-S10 (1994). 6 pages.
Fasano, et. al., "Vibrio cholerae produces a second enterotoxin, which affects intestinal tight junctions" Proc. Nat. Acad. Sci. USA, 88: 5242-5246 (1991).
Filikov, et. al., "Structure-based design of ligands for protein basic domains: application to the HIV-1 Tat protein." J. Comput. Aided Mol. Des.12(3): 229-240 (1998).
Fiorentini, et. al., "Clostridium difficile toxin A and its effects on cells." Toxicon, 29(6): 543-567 (1991).
Fox, "Developments in parathyroid hormone and related peptides as bone-formation agents." Curr. Opin. Pharmacol., 2: 338-344 (2002).
Fricker et al. "Permeation enhancement of octreotide by specific bile salts in rats and human subjects: in vitro, in vivo correlations", British Journal of Pharmacology (1996) vol. 117, pp. 217-223.
"FSRH Guideline: Combined Hormonal Contraception," The Faculty of Sexual & Reproductive Healthcare, 2019, pp. 1-108.
Geer, Richard J. et al. "Efficacy of octreotide acetate in treatment of severe postgastrectomy dumping syndrome." Annals of Surgery 212.6 (1990): 678. 10 pages.
Gillis et al., "Octreotide long-acting release (LAR)," Drugs (1997) vol. 53, No. 4, pp. 681-699.
Giustina et al. "A consensus on the medical treatment of acromegaly" Nature Reviews Endocrinology (2014) vol. 10, pp. 243-248.
Grasso et al., "Investigational therapies for acromegaly", Expert Opinion on Investigational Drugs, (2013), 22: 8, pp. 955-963.
Gumbiner, "Structure, biochemistry, and assembly of epithelial tight junctions." Am. J. Physiol., 253: C749-C758 (1987).
Hecht, et. al., "Clostridium difficile toxin A perturbs cytoskeletal structure and tight junction permeability of cultured human intestinal epithelial monolayers." J. Clin. Invest., 82: 1516-1524 (1988).
Hemingway et al. "The effects of sandostatin (Octreotide, SMS 201-995) infusion on splanchnic and hepatic blood now in an experimental model of hepatic metastases" Br. J. Cancer (1992) vol. 65, pp. 396-398.
Higgins et al., "The Sexual Acceptability of Contraception: Reviewing the Literature and Building a New Concept," J. Sex Res., 2016, 52(4-5): 417-456.
Higham, C.E. et al., "Effective combination treatment with cabergoline and low-dose pegvisomant in active acromegaly: a prospective clinical trial", The Journal of Clinical Endocrinology & Metabolism, Jan. 25, 2012, vol. 97(4), pp. 1187-1193.
Hoeldtke, RD et al., "Treatment of Orthostatic Hypotension with Octreotide," Journal of Clinical Endocrinology and Metabolism, The Endocrine Society, vol. 68, No. 6, Jun. 1989, pp. 1051-1059.
Hsi-U I Ho et al., "Preparation of microemulsions using polyglycerol fatty acid esters as surfactant for the delivery of protein drugs". Journal of Pharmaceutical Sciences, American Pharmaceutical Association, Washington, US, vol. 85, No. 2, pp. 138-143, 1996.
Huffman, F.G., et al., "L-Glutamine Supplementation Improves Nelfinavir-Associated Diarrhea in HIV-Infected Individuals," HIV clinical trials, Feb. 2, 2015, vol. 4(5), pp. 324-329.
International Preliminary Report on Patentability from International Application Serial No. PCT/IB07/04569 issued Nov. 3, 2009, 6 pages.
International Search Report and Written Opinion from international patent application No. PCT/IB07/04569, dated Oct. 20, 2009, 6 pages.
International Search Report and Written Opinion from PCT Application No. PCT/US2015/065006, dated Feb. 23, 2016, 9 pages.
International Search Report and Written Opinion of the International Searching Authority for PCT/US2016/016384, mailed Apr. 22, 2016, 7 pages.
International Search Report and Written Opinion of the International Searching Authority for PCT/US2017/014379, mailed Apr. 7, 2017, 15 pages.
International Search Report dated Mar. 18, 2010 in WO application-PCT/IB09/07155, 3 pages.
International Search Report from international patent application No. PCT/IB2005/004183, dated Oct. 19, 2006, 8 pages.
IOM (Institute of Medicine), A Review of the HHS Family Planning Program: Mission, Management, and Measurement of Results. Washington, DC: The National Academies Press. 2009, 1-487.
Irving et al. "Therapeutic value of octreotide for patients with severe dumping syndrome—a review of randomised controlled trials." Postgrad Med J, 2001, vol. 77, pp. 441-442 (2001).
Isaacson, "Managed Care Approach to the Treatment of Neurogenic Orthostatic Hypotension," The American Journal of Managed Care, Oct. 2015, pp. S258-S268. 11 pages.
Jackson, "Drug Transport Across Gastrointestinal Epithelia", Physiology of the Gastrointestinal Tract, 2nd Ed., Johnson, ed., Raven Press, New York, Chapter 59, 2: 1597-1621 (1987).

(56) References Cited

OTHER PUBLICATIONS

Jansen et al., "Postprandial Hypotension: Epidemiology, Pathophysiology, and Clinical Management," Annals of Internal Medicine, 1995, vol. 122, No. 4, pp. 286-295.
Jenkins et al. "Pharmacokinetics of Octreotide in Patients with Cirrhosis and Portal Hypertension; Relationship Between the Plasma Levels of the Analogue and the Magnitude and Duration of the Reduction in Corrected Wedged Hepatic Venous Pressure", HPB Surgery (1998) vol. 11, pp. 13-21.
Jenkins et al. "Randomised trial of octreotide for long term management of cirrhosis after variceal haemorrhage", BMJ (1997) vol. 315, pp. 1338-1341.
Jeppesen, P.B., et al., "Teduglutide, a Novel Glucagon-like Peptide 2 Analog, in the Treatment of Patients With Short Bowel Syndrome," Therapeutic advances in gastroenterology, Feb. 15, 2012, vol. 5(3), pp. 159-171.
Jiao, et. al., "In vitro and in vivo evaluation of oral heparin-loaded polymeric nanoparticles in rabbits", Circulation, 105:230-235 (2002).
Katznelson et al. "Acromegaly: an endocrine society clinical practice guideline." Journal of Clinical Endocrinology and Metabolism (2014): vol. 99, No. 11, 3933-3951.
Kohler, E. et al. "Absorption of an aqueous solution of a new synthetic somatostatin analogue administered to man by gavage", European journal of clinical pharmacology 33.2 (1987): 167-171.
Kulke, M.H., et al., "Telotristat Etiprate, a Novel Serotonin Synthesis Inhibitor, in Patients with—Carcinoid Syndrome and Diarrhea Not Adequately Controlled by Octreotide," Endocrine Related Cancer, Oct. 2014, vol. 21(5), pp. 705-714.
Lancranjan, I. et al. "Sandostatin® LAR®: A Promising Therapeutic Tool in the Management of Acromegalic Patients," Metabolism, 1996, 45(8): 1, 67-71.
Lancranjan, I. et al. "Results of a European Multicentre Study with Sandostatin® LAR® in Agromegalic Patients" Pituitary 1999, 1: 105-114.
Lariviere, W., et al., "Novel therapeutic approaches to autosomal dominant polycystic kidney disease," Transl Res, 2015, 165(4): 488-98.
Le Tourneau, Christophe, et al., "Dose escalation methods in phase 1 cancer clinical trials", J Natl Cancer Inst, May 20, 2009; 101(10): 708-20, Epub May 12, 2009.
Lin et al., "Haemodynamic effects of 8-day octreotide and prazosin administration in portal hypertensive rats." European Journal of Clinical Investigation, 28 (8), 622-628. (1998). 1365-2362.
Lueck, Christian J., and Gawn G. McIlwaine. "Interventions for idiopathic intracranial hypertension." The Cochrane Library (2009). 14 pages.
Lustig, R. H., et al. "A multicenter, randomized, double-blind, placebo-controlled, dose-finding trial of a long-acting formulation of octreotide in promoting weight loss in obese adults with insulin hypersecretion." International Journal of Obesity 30.2 (2006): 331-341.
Madara, "Loosening Tight Junctions: Lessons from the Intestine," J Clin Invest, Apr. 1989; 83(4): 1089-1094.
Madsen, M. et al., "Cotreatment with pegvisomant and a somatostatin analog (SA) in SA-responsive acromegalic patients", The Journal of Clinical Endocrinology & Metabolism, Jun. 1, 2011, vol. 96(8), pp. 2405-2413.
Manjila et al. "Pharmacological management of acromegaly: a current perspective." Neurological Focus (2010): vol. 29. No. 4, 1-9.
Manning et al. "Oxytocin and Vasopressin Agonists and Antagonists as Research Tools and Potential Therapeutics," Journal of Neuroendocrinology, 2012, 24: 609-628.
McCormick, P. Aiden, et al. "Cardiovascular effects of octreotide in patients with hepatic cirrhosis." Hepatology 21.5 (1995): 1255-1260.
Melmed, Shlomo et al. "Safety and efficacy of oral octreotide in acromegaly: results of a multicenter phase III trial" J. Clin. Endocrinol. Metab. 100.4 (2015): 1699-1708. & Erratum to: "Safety and Efficacy of Oral Octreotide in Acromegaly: Results of a Multicenter Phase III Trial" J. Clin. Endocrinol. Metab., vol. 105, Issue 12, Dec. 2020, p. e4986. 12 pages.
Melmed, S. et al. "OR17-5: Efficacy and Safety of Oral Octreotide in Acromegaly: Results of a Multicenter Phase III Trial in 155 Patients" Abstracts—Orals, Poster Preview Presentations, and Posters, OR17-From Genetics to Clinical Trials in Pituitary Disease Clinical/Translational, Sunday, Jun. 22, 2014; 96th Annual Meeting and Expo of the Endocrine Society, Chicago, IL, Jun. 21-24, 2014; 2 pages.
Melmed, Shlomo. "New therapeutic agents for acromegaly." Nature Reviews Endocrinology 12.2 (2016): 90-98; Advanced online publication Nature Reviews Endocrinology Nov. 27, 2015, pp. 1-9.
Mimuro et al., "The somatostatin analogue, octreotide, modifies both steroidogenesis and IGFBP-1 secretion in human utenizing granulosa cells", Human Reproduction, 1998, 13(1): 150-150.
Moller, Soren, et al. "Effect of octreotide on systemic, central, and splanchnic haemodynamics in cirrhosis", Journal pf Hepatology 26.5 (1997): 1026-1033.
Moreau et al. "Comparison of the effect of terlipressin and albumin on arterial blood volume in patients with cirrhosis and tense ascites treated by paracentesis: a randomised pilot study", Gut, 2002, 50: 90-94.
Moreland, "Rheumatology and Immunology Therapy: A-Z essentials," (2004) Springer Science & Business Media, pp. 13. 2 pages.
Mycapssa™ (Formerly Octreolin™) Efficacy and Safety of Octreotide for Acromegaly, History of Changes for Study: NCT01412424, 2017, U.S. National Library of Medicine, ClinicalTrials.gov, 16 pages.
Mycapsssa® (octreotide) delayed-release capsules for oral use, Prescribing Information, Chiasma, 2020, pp. 1-17.
Nardone et al., "The efficacy of octreotide therapy in chronic bleeding due to vascular abnormalities of the gastrointestinal tract." Aliment Pharmacology & Therapeutics, 13(11), pp. 1429-1436 (1999).
Neggers, et al., "Long-term efficacy and safety of combined treatment of somatostatin analogs and pegvisomant in acromegaly", J Clin Endocrinol Metab, Dec. 2007; 92(12): 4598-601.
Neggers et at "Long-Term efficacy and safety of pegvisomant in combination with long-acting somatostatin analogs in acromegaly", Journal of Clinical Endocrinology and Metabolism (2014): vol. 99, No. 10, 3644-3652.
Newman, C.B. et al., "Octreotide as Primary Therapy for Acromegaly", J Clin Endocrinol MEtab, 83, pp. 3034-3040, 1998.
Nir et al, "Fear of injections in young adults; prevalence and associations", Am. J. Trop. Med. Hyg., 68(3), pp. 341-344 (2003).
"Octreotide for a Possible Cure for IIH" Facebook; Retrieved from www.facebook.com/pages/Octreotide-for-a-possible-Cure-for-IIH, on Mar. 3, 2015. 5 pages.
Ouyang, et al., "Structure-activity relationship for enhancement of paracellular permeability across Caco-2 cell monolayers by 3-alkylamido-2-alkoxypropylphosphocholines", J. Med. Chem. 45(13): 2857-2866 (2002).
Panagopoulos, G. N., et al. "Octreotide: a therapeutic option for idiopathic intracranial hypertension", Neurol Neurophysiol Neurosci, 1 (2007): 1-6.
Prescribing information for Sandostatin LAR Sep. 2011, Novartis, 17 pages.
Rebouche, "Carnitine absorption: effects of sodium valproate and sodium actanoate in the caco-2 cell culture model of human intenstinal epithelium", L. Nutr. Biochem., vol. 9, pp. 228-235 (Apr. 1998).
Reid, Tirissa J. et al., fIIgf-1 levels across the spectrum of normal to elevated in acromegaly: relationship to insulin sensitivity, markers of cardiovascular risk and body composition, Pituitary (2015) pp. 808-819.
Ruggenenti et al., "Safety and efficacy of long-acting somatostatin treatment in autosomal-dominant polycystic kidney disease", Kidney International, vol. 68, 2005, pp. 206-216.
Sanchez, George A., Nisa Kubiliun, and Jamie S. Barkin. "Variceal bleeding and long-acting octreotide: a new addition to the armamentarium?" Digestive diseases and sciences 53.11 (2008): 3046-3047.

(56) References Cited

OTHER PUBLICATIONS

Sandostatin® Lar Depot (octreotide acetate) for injectable suspension, Prescribing Information, Novartis Pharmaceuticals Corporation, 2019, pp. 1-21.
Sandostatin (octreotide acetate), Prescribing Information, as approved by the FDA; initial U.S. Approval 1988; Novartis; Retrieved from the Internet (URL):https://accessdata.fda.gov/drugsatfda_docs/abel/2010/019667s058,021008s023lbl.pdf, 29, pages.
Schilfgaarde, et. al., "Cloning of genes of nontypeable Haemophilus influenzae involved in penetration between human lung epithelial cells", Infect. Immun.68(8): 4616-4623 (2000).
Search Report for CN 200980140593.9 dated Mar. 12, 2013, 2 pages.
Shimon et al. "Estrogen treatment for acromegaly", Pituitary (2012): vol. 15, No. 4, pp. 601-607.
Spahr, Laurent, et al. RA 3-month course of long-acting repeatable octreotide (sandostatin LAR) improves portal hypertension in patients with cirrhosis: a randomized controlled study, The American Journal of Gastroenterology 102.7 (2007): 1397-1405.
Strasburer et al., "Patient-reported outcomes of parenteral somatostatin analogue injections in 195 patients with acromegaly", European Journal of Endocrinology, 2016, 174: 355-362.
Suda et al. "Efficacy of combined octreotide and cabergoline treatment in patients with acromegaly: a retrospective clinical study and review of the literature", Endocrine Journal (2013): vol. 60, No. 4, 507-515.
Thanou, M., et al. "Intestinal absorption of octreotide: N-trimethyl chitosan chloride (TMC) ameliorates the permeability and absorption properties of the somatostatin analogue in vitro and in vivo", Journal of pharmaceutical Sciences 89.7 (2000): 951-957.
Thanou, Maya, et al. "Intestinal absorption of octreotide using trimethyl chitosan chloride: studies in pigs", Pharmaceutical research 18 .6 (2001): 823-828.
Tuvia, et al., "A Novel Suspension Formulation Enhances Intestinal Absorption of Macromolecules Via Transient and Reversible Transport Mechanisms", Pharm Res. (Feb. 21, 2014); 31(8): 2010-2021.
Tuvia, S., et al., "Oral Octreotide Absorption in Human Subjects: Comparable Pharmacokinetics to Parenteral Octreotide and Effective Growth Hormone Suppression", The Journal of Clinical Endocrinology & Metabolism, Jul. 1, 2012, vol. 97(7), pp. 2362-2369.
Vallette et al., "Oral estroprogestin: an alternative low cost therapy for women with postoperative persistent acromegaly?" Pituitary, 2010, 13: 311-314.
Vance, M.L. et al., "Long-term Treatment of 189 Acromegalic Patients with the Somatostatin Analog Octreotide", Arch Intern Med, 151, pp. 1573-1576, 1991.
Vinken et al. "Fulminant eosinophilic myocarditis leading to sudden death in a young acromegalic woman", Acta Clin Belg, Sep.-Oct. 2005; 60(5): 253-5.
Vorobioff, Julio D., et al. "Octreotide enhances portal pressure reduction induced by propranolol in cirrhosis: a randomized, controlled trial", The American journal of gastroenterology 102.10 (2007): 2206-2213.
Walpole et al., "The weight of nations: an estimation of adult human biomass", BMC Public Health, 2012, vol. 12, p. 439. 6 pages.
Wang, et. al., "Increasing epithelial junction permeability enhances gene transfer to airway epithelia in vivo", Am. J. Respir. Cell Mol. Biol., 22: 129-138 (2000).
Watnasirichaikul, et. al., "In-vitro release and oral bioactivity of insulin in diabetic rats using nanocapsules dispersed in biocompatible microemulsion", J. Pharm. Pharmacol., 54(4): 473-480 (2002).
Watnasirichaikul S. et al, "Preparation of biodegradable insulin nanocapsules from biocompatible microemulsions", Pharmaceutical Research, vol. 17, No. 6, p. 684-689 (2000).
Williams, G., et al. "Effective and lasting growth-hormone suppression in active acromegaly with oral administration pf somatostatin analogue SMS 201-995", The Lancet 328.8510 (1986): 774-778.
Wolf, David C. "The management of variceal bleeding: past, present and future", The Mount Sinai journal of medicine, New York 66.1 (1999): 1-13.
Wolin, E.M., et al., "Safety, Tolerability, Pharmacokinetics, and Pharmacodynamics of a Long-acting Release (LAR) Formulation of Pasireotide (SOM230) in Patients With Gastroenteropancreatic Neuroendocrine Tumors: Results From a Randomized, Multicenter, Open-label, Phase I Study," Cancer Chemotherapy and Pharmacology, 2013, vol. 72(2), pp. 387-395.
Wright et al., "Fear of needles-nature and prevalence in general practice", Australian family physician, 38(3) Mar. 2003. 4 pages.
Written Opinion in International Application No. PCT/IB09/07155, dated Mar. 18, 2010, 8 pages.
Written Opinion of the International Searching Authority for corresponding international patent application PCT/IB2005/004183, dated Oct. 19, 2006, 11 pages.
Yowell, et. al., "Novel Effects with Polyethylene glycol modified pharmaceuticals", Cancer Treat. Rev., 28(Suppl. A): 3-6 (2002). 5 pages.
Zavoico, et. al., "Perturbation of egg phosphatidylcholine and dipalmitoylphosphatidylcholine multilamellar vesicles by n-alkanols. A fluorescent probe study." Biochimica et Biophysica Acta, 812(2): 299-312 (1985).
Zidan, J., et al. "Octreotide in the treatment of severe chemotherapy-induced diarrhea." Annals of oncology 12.2 (2001): 227-229.
Alexopoulou et al., "Efficacy and tolerability of lanreotide Autogel therapy in acromegalic patients previously treated with octreotide LAR", Eur J Endocrinol. Sep. 2004;151(3): 317-24. doi:10.1530/eje.0.1510317.
[Author Unknown] "The Seventh Report of the Joint National Committee on Prevention, Detection, Evaluation, and Treatment of High Blood Pressure (JNC 7 Express)", U.S. Department of Health and Human Services, National Institutes of Health, National Heart, Lung, and Blood Institute, National High Blood Pressure Education Program, NIH publication No. 03-5233 (Dec. 2003); pp. 1-52.
Ayuk, J., et al., "Growth hormone and pituitary radiotherapy, but not serum insulin-like growth factor-I concentrations, predict excess mortality in patients with acromegaly." J Clin Endocrinol Metab 2004; 89: 1613-1617.
Barkan AL, et al., "Plasma insulin-like growth factor-1/somatomedin-C in acromegaly: correlation with the degree of growth hormone hypersecretion." J Clin Endocrinol Metab. Jul. 1988; 67(1): 69-73. doi: 10.1210/jcem-67-1-69.
Bauer W, et al., "SMS 201-995: a very potent and selective octapeptide analogue of somatostatin with prolonged action." Life Sci 1982; 31: 1133-1140.
Beerman, et al., "Pharmacokinetics of Lisinopril (IV/PO) in Healthy Volunteers", Biopharmaceutics & Drug Disposition (1989); 10: 397-409.
Benson et al., "Recommended guidelines for the treatment of cancer treatment-induced diarrhea." J Clin Oncol. Jul. 15, 2004; 22(14): 2918-26. doi: 10.1200/JCO.2004.04.132.
Bidlingmaier M, et al., "Reference intervals for insulin-like growth factor-1 (igf-i) from birth to senescence: results from a multicenter study using a new automated chemiluminescence IGF-I immunoassay conforming to recent international recommendations." J Clin Endocrinol Metab. May 2014; 99(5): 1712-21. doi: 10.1210/jc.2013-3059. Epub Feb. 27, 2014.
Biermasz NR, et al., "Sandostatin LAR in acromegaly: a 6-week injection interval suppresses GH secretion as effectively as a 4-week interval." Clin Endocrinol (Oxf) 2003; 58: 288-295.
Burgers AM, et al., "Meta-analysis and dose-response metaregression: circulating insulin-like growth factor I (IGF-I) and mortality." J Clin Endocrinol Metab 2011; 96: 2912-2920.
Byrne et al., "Growth hormone, glutamine, and a modified diet enhance nutrient absorption in patients with severe short bowel syndrome." JPEN J Parenter Enteral Nutr. Jul.-Aug. 1995; 19(4): 296-302. doi: 10.1177/0148607195019004296.
Cano-Cebrian et al., "Intestinal Absorption Enhancement Via the Paracellular Route by Fatty Acids, Chitosans and Others: A Target for Drug Delivery." Curr Drug Deliv. Jan. 2005; 2(1): 9-22. doi: 10.2174/1567201052772834.
Center For Drug Evaluation And Research, Application No. 208401Orig1s000, Clinical Pharmacology And Biopharmaceutics Review(s), NDA No. 208401, Reference ID: 3907124 (Submission

(56) References Cited

OTHER PUBLICATIONS

Date: Jun. 30, 2015) [online] https://www.accessdata.fda.gov/drugsatfda_docs/nda/2016/208401Orig1s000ClinPharmR.pdf(Access Date: Oct. 26, 2021); 32 pages.
Chandok, Natasha, "Polycystic liver disease: a clinical review," Ann Hepatol. Nov.-Dec. 2012; 11(6): 819-26.
Chanson, P., et al., "Control of IGF-I levels with titrated dosing of lanreotide Autogel over 48 weeks in patients with acromegaly." Clin Endocrinol (Oxf) 2008; 69: 299-305.
Chapman et al., "Autosomal-dominant polycystic kidney disease (ADPKD): executive summary from a Kidney Disease: Improving Global Outcomes (KDIGO) Controversies Conference." Kidney Int. Jul. 2015; 88(1): 17-27. doi: 10.1038/ki.2015.59. Epub Mar. 18, 2015.
Chieffo C, et al., "Efficacy and safety of an octreotide implant in the treatment of patients with acromegaly." J Clin Endocrinol Metab 2013; 98: 4047-4054.
Clemmons DR. et al., "Consensus statement on the standardization and evaluation of growth hormone and insulin-like growth factor assays." Clin Chem 2011; 57: 555-559.
Cnossen et al., "Polycystic liver disease: an overview of pathogenesis, clinical manifestations and management." Orphanet J Rare Dis. May 1, 2014: 9: 69. doi: 10.1186/1750-1172-9-69. 13 pages.
Colao A, et al., "Systemic complications of acromegaly: epidemiology, pathogenesis, and management." Endocr Rev 2004; 25: 102-152.
Collier, et al., "Pharmacokinetic profile of oral digoxin in healthy volunteers", International Journal of Pharmaceutics (1978); 1: 3-14.
Cozzi R, et al., "Primary treatment of acromegaly with octreotide LAR: a long-term (up to nine years) prospective study of its efficacy in the control of disease activity and tumor shrinkage." J Clin Endocrinol Metab 2006; 91: 1397-1403.
Dasari and Yao, "Initial treatment of well-differentiated neuroendocrine tumors." Oncology (Williston Park). Nov. 2014; 28(11): 945-7.
Dekkers OM, et al., "Mortality in acromegaly: a metaanalysis." J Clin Endocrinol Metab 2008; 93: 61-67.
Didden et al., "Octreotide therapy in dumping syndrome: Analysis of long-term results." Aliment Pharmacol Ther. Nov. 1, 2006; 24(9): 1367-75. doi: 10.1111/j.1365-2036.2006.03124.x.
Doligalski et al., "Drug interactions: a primer for the gastroenterologist." Gastroenterol Hepatol (NY). Jun. 2012; 8(6): 376-83.
DrugBank Online, "Digoxin", Accession No. D800390 [online] https://go.drugbank.com/drugs/DB00104 (Access Date: Mar. 4, 2021); 15 pages.
Edling, K. and Heaney, A., "An update on the treatment of acromegaly." Research and Reports in Endocrine Disorders 2013: 3 1-11.
Fleseriu, M. "Clinical efficacy and safety results for dose escalation of somatostatin receptor ligands in patients with acromegaly: a literature review." Pituitary 2011; 14: 184-193.
Freda Pu, "Somatostatin analogs in acromegaly." J Clin Endocrinol Metab 2002; 87: 3013-3018.
Gambineri, "Efficacy of Octreotide-LAR in Dieting Women with Abdominal Obesity and Polycystic Ovary Syndrome." J Clin Endocrinol Metab. Jul. 2005; 90(7): 3854-62. doi: 10.1210/jc.2004-2490. Epub Apr. 12, 2005.
Giustina A, et al., "Pathophysiology of the neuroregulation of growth hormone secretion in experimental animals and the human." Endocr Rev 1998; 19: 717-79.
Higham et al., "Long-term experience of pegvisomant therapy as a treatment for acromegaly." Clin Endocrinol (Oxf). Jul. 2009;71(1): 86-91. doi:10.1111/j.1365-2265.2008.03469.x. Epub Nov. 5, 2008.
Holdaway, IM, et al., "A meta-analysis of the effect of lowering serum levels of GH and IGF-I on mortality in acromegaly." Eur J Endocrinol 2008; 159: 89-95.
Humphries and Merritt, "Review article: drug interactions with agents used to treat acid-related diseases." Aliment Pharmacol Ther. Aug. 1999: 13 Suppl 3: 18-26. doi: 10.1046/j.1365-2036.1999.00021.x.

International Search Report and Written Opinion for International Application No. PCT/US2023/063219, mailed on Jun. 13, 2023, 10 pages.
Jane, JA, Jr., et al., "Endoscopic transsphenoidal surgery for acromegaly: remission using modem criteria, complications, and predictors of outcome." J Clin Endocrinol Metab 2011; 96: 2732-2740.
Jeppesen, "Teduglutide (ALX-0600), a dipeptidyl peptidase IV resistant glucagon-like peptide 2 analogue, improves intestinal function in short bowel syndrome patients." Gut. Sep. 2005; 54(9): 1224-31. doi: 10.1136/gut.2004.061440.
Juckett and Trevdi, "Evaluation of chronic diarrhea." Am Fam Physician. Nov. 15, 2011; 84(10): 1119-26.
Kloppel et al., "The gastroenteropancreatic neuroendocrine cell system and its tumors: the WHO classification." Ann N Y Acad Sci. Apr. 2004: 1014: 13-27. doi: 10.1196/annals.1294.002.
Lamberts, SW, et al., "Longterm treatment of acromegaly with the somatostatin analogue SMS 201-995." N Engl JMed 1985; 313: 1576-1580.
Lamberts, SW, et al., "The somatostatin analog SMS 201-995 induces long-acting inhibition of growth hormone secretion without rebound hypersecretion in acromegalic patients." J Clin Endocrinol Metab 1985; 60: 1161-1165.
Lanoxin® (digoxin) Tablets, USP, 125 mcg (0.125 mg) Scored I.D. Imprint Y3B (yellow), 250 mcg (0.25 mg) Scored I.D. Imprint X3A (white), Prescribing Information, Revised Date: Nov. 2011, Reference ID: 3043958, Manufactured for GlaxoSmithKline, Research Triangle Park, NC 27709; 19 pages.
Lee CC, et al., "Stereotactic radiosurgery for acromegaly." J Clin Endocrinol Metab 2014; 99: 1273-1281.
Lisk, "Postprandial hypotension." GM Journal, Apr. 2010, 42: 203-206.
Lubart et al. "Postprandial Hypotension in Long-Term Care Elderly Patients on Enteral Feeding." Journal of the American Geriatrics Society, Sep. 2006, vol. 54, Issue 9, pp. 1377-1381.
MacArthur and Dupont, "Etiology and pharmacologic management of noninfectious diarrhea in HIV-infected individuals in the highly active antiretroviral therapy era." Clin Infect Dis. Sep. 2012; 55(6): 860-7. doi: 10.1093/cid/cis544. Epub Jun. 14, 2012.
Maggio et al., "Oral delivery of octreotide acetate in Intravail(R) improves uptake, half-life, and bioavailability over subcutaneous administration in male Swiss webster mice." Regul Pept 2011; 167: 233-238.
Manolopoulou J, et al., "Automated 22-kD growth hormone-specific assay without interference from Pegvisomant." Clin Chem 2012; 58: 1446-1456.
Melmed et al., "Current Treatment Guidelines for Acromegaly." J Clin Endocrinol Metab. Aug. 1998; 83(8): 2646-52. doi: 10.1210/jcem.83.8.4995.
Melmed, S. Acromegaly pathogenesis and treatment. J Clin Invest 2009; 119: 3189-3202.
Melmed, S. "Medical progress: Acromegaly." N Engl J Med 2006; 355: 2558-2573.
Murray RD, et al., "Central and peripheral actions of somatostatin on the growth hormone-IGF-I axis." J Clin Invest 2004; 114: 349-356.
Nehra et al., "An open trial of octreotide long-acting release in the management of short bowel syndrome." Am J Gastroenterol. May 2001;96(5): 1494-8. doi: 10.1111/j.1572-0241.2001.03803.x.
Nguyen, et al., "Digoxin Use in Modern Medicine", US Pharmacist (Feb. 2015); 40(2): 44-48.
Oberg et al., "Consensus report on the use of somatostatin analogs for the management of neuroendocrine tumors of the gastroenteropancreatic system." Ann Oncol. Jun. 2004; 15(6): 966-73.
Oberg et al., "Neuroendocrine gastro-entero-pancreatic tumors: ESMO Clinical Practice Guidelines for diagnosis, treatment and follow-up." Ann Oncol. Oct. 2012: 23 Suppl 7: vii 124-30.
Pasquali, "Polycystic ovary syndrome: a multifaceted disease from adolescence to adult age," Ann N Y Acad Sci. Dec. 2006: 1092: 158-74. doi: 10.1196/annals.1365.014.
Pavel et al., "Effect of everolimus on the pharmacokinetics of octreotide long-acting repeatable in patients with advanced neuroendocrine tumors: An analysis of the randomized phase III

(56) References Cited

OTHER PUBLICATIONS

RADIANT-2 trial." Clin Pharmacol Ther. Apr. 2017; 101(4): 462-468. doi: 10.1002/cpt.559. Epub Dec. 29, 2016.

Pokrajac A, et al., "Pituitary-independent effect of octreotide on IGF-I generation." European Journal of Endocrinology (2009) 160 543-548.

Prescribing Label for Mycapssa®, (octreotide) delayed-release capsules, for oral use Initial U.S. Approval: 1988. Chiasma, revised Jun. 2020. 20 pages.

Reutens AT, et al., "Evaluation and application of a highly sensitive assay for serum growth hormone (GH) in the study of adult GH deficiency." J Clin Endocrinol Metab 1995; 80: 480-485.

Ribeiro-Oliveira, A, Jr., et al., "The changing face of acromegaly—advances in diagnosis and treatment." Nat Rev Endocrinol 2012; 8: 605-611.

Salvatori et al., "Lanreotide extended-release aqueous-gel formulation, injected by patient, partner or healthcare provider in patients with acromegaly in the United States: 1-year data from the SODA registry." Pituitary. Feb. 2014; 17(1): 13-21. doi: 10.1007/s11102-012-0460-2.

Salvatori et at., "Effectiveness of self- or partner-administration of an extended-release aqueous-gel formulation of lanreotide in lanreotide-naïve patients with acromegaly." Pituitary. Jun. 2010; 13(2): 115-22. doi: 10.1007/s11102-009-0207-x.

Schmidt et al., "Well-differentiated neuroendocrine tumors: a review covering basic principles to loco-regional and targeted therapies," Oncogene. Mar. 31, 2011; 30(13): 1497-505. doi: 10.1038/onc.2010.548. Epub Dec. 6, 2010.

Shaunfield, S., et al., "Development of the Functional Assessment of Cancer Therapy-Carcinoid Syndrome Symptom Index." Neuroendocrinology. 2021; 111(9): 850-862. doi: 10.1159/000511482. Epub Sep. 10, 2020.

Sherlock M, et al., "A paradigm shift in the monitoring of patients with acromegaly: last available growth hormone may overestimate risk." J Clin Endocrinol Metab 2014; 99: 478-485.

Sherlock M, et al., "Medical therapy in acromegaly." Nat Rev Endocrinol 2011; 7: 291-300.

Shimon, I, et al., "Somatostatin receptor (SSTR) subtype-selective analogues differentially suppress in vitro growth hormone and prolactin in human pituitary adenomas. Novel potential therapy for functional pituitary tumors." J Clin Invest 1997; 100: 2386-2392.

Stewart PM, et al., "Clinical and biochemical response following withdrawal of a long-acting, depot injection form of octreotide (Sandostatin-LAR)." Clin Endocrinol (Oxf) 1999; 50: 295-299.

Strosberg et al., "Phase 3 Trial of 177Lu-Dotatate for Midgut Neuroendocrine Tumors." N Engl J Med. Jan. 12, 2017; 376(2): 125-135. doi: 10.1056/NEJMoa1607427.

Strosberg, "Systemic treatment of gastroenteropancreatic neuroendocrine tumors (GEP-NETS): current approaches and future options." Endocr Pract. Feb. 2014; 20(2):167-75. doi: 10.4158/EP13262.RA.

Szilagyi and Shrier, "Systematic review: the use of somatostatin or octreotide in refractory diarrhoea." Aliment Pharmacol Ther. Dec. 2001; 15(12): 1889-97.

Thiagarajah et al., "Secretory diarrhoea: mechanisms and emerging therapies." Nat Rev Gastroenterol Hepatol. Aug. 2015; 12(8): 446-57. doi:10.1038/nrgastro.2015.111. Epub Jun. 30, 2015.

Turner, HE, et al., "Systematic dose-extension of octreotide LAR: the importance of individual tailoring of treatment in patients with acromegaly." Clin Endocrinol (Oxf) 2004; 61: 224-231.

U.S. Department of Health and Human Services, "Guidance for Industry Food-Effect Bioavailability and Fed Bioequivalence Studies." U.S. Department of Health and Human Services Food and Drug Administration Center for Drug Evaluation and Research (CDER), Dec. 2002. 12 pages.

Van Der Lely AJ, et al., "Long-term safety of pegvisomant in patients with acromegaly: comprehensive review of 1288 subjects in Acrostudy." J Clin Endocrinol Metab 2012; 97: 1589-1597.

Wass JA. "Octreotide treatment of acromegaly." Horm Res 1990; 33 Suppl 1:1-5; discussion 6. 6 pages.

Zestril® (lisinopril) tablets, for oral use, Tablets: 2.5 mg, 5 mg, 10 mg, 20 mg, 30 mg, 40 mg, Label; Highlights of Prescribing Information, Patient Counseling Information approved by the U.S. Food and Drug Administration; Revised: Dec. 2014 (Dec. 2014), Initial U.S. Approval: 1988, Reference ID: 3678295, Distributed by: AstraZeneca Pharmaceuticals LP Wilmington, DE 19850 AstraZeneca, 16 pages.

* cited by examiner

METHOD OF TREATING DISEASES

RELATED APPLICATIONS

This application is a continuation of U.S. patent application Ser. No. 18/514,644, filed Nov. 20, 2023, which is a continuation of U.S. patent application Ser. No. 17/721,725, now U.S. Pat. No. 11,857,595, filed Apr. 15, 2022, which is a continuation of U.S. patent application Ser. No. 17/094,238, now U.S. Pat. No. 11,338,011, filed Nov. 10, 2020, which is a continuation of U.S. patent application Ser. No. 16/881,348, now U.S. Pat. No. 11,052,126, filed on May 22, 2020, which is a continuation of U.S. patent application Ser. No. 16/233,749, now U.S. Pat. No. 10,695,397, filed on Dec. 27, 2018, which is a continuation of U.S. patent application Ser. No. 15/014,634, now U.S. Pat. No. 10,238,709, filed on Feb. 3, 2016, which claims priority under 35 U.S.C. 119(e) to U.S. Provisional Patent Application Ser. No. 62/111,369, filed on Feb. 3, 2015 and U.S. Provisional Patent Application Ser. No. 62/136,012, filed Mar. 20, 2015, the contents of each of which is hereby incorporated herein by reference in its entirety.

FIELD OF THE TECHNOLOGY

The present invention relates to oral drug delivery of octreotide for treating diseases.

BACKGROUND

Acromegaly, usually caused by a growth hormone-secreting pituitary adenoma, is an inexorable chronic condition with significant morbidity and mortality (1). Hypersecretion of both GH and its target hormone, IGF-I, leads to acral disfigurement with bony overgrowth, hypertension, cardiac, cerebrovascular, and respiratory disease, arthritis and tissue swelling (2,3). In addition to pituitary tumor growth and/or post-surgical recurrence, acromegaly co-morbidities occur especially with uncontrolled GH/IGF-I hypersecretion, and most are ameliorated by aggressively controlling GH/IGF-I levels(4-6). Acromegaly mortality determinants include GH>2.5 ng/mL and elevated IGF-I, hypertension, cardiovascular and cerebrovascular disease, requirement for glucocorticoid replacement and prior pituitary radiation (4, 5, 7, 8). Effective surgical, radiation and medical strategies to improve co-morbidity and mortality require control of GH/IGF-I (9-11)-(12,13). Treatments exhibit patient-specific efficacy and each manifests unique side effects (1,14-16).

Somatostatin inhibits pituitary GH secretion (17). Octreotide was selected as a therapeutic because of its prolonged circulating half-life compared to native somatostatin (2 hours vs. 2 minutes)(18), as well as the absence of acute rebound GH hypersecretion (19,20). Injections of somatostatin analogs acting as receptor ligands, also termed somatostatin receptor ligands (SRL) include subcutaneous immediate release, intramuscular or deep subcutaneous depot preparations of octreotide and lanreotide (16,21-23). Both target mainly somatotroph SSTR2 receptors to suppress GH secretion and subsequent peripheral IGF-I production (17,24,25). Currently available parenteral SRLs effectively achieve biochemical control and symptomatic improvement in acromegaly, yet these discomforting injections engender challenges to patients and health care providers. Although attempts to develop oral octreotide have been reported (26) (27), these formulations were not assessed further.

Idiopathic intracranial hypertension (IIH), sometimes called by the older names benign intracranial hypertension (BIH) or pseudotumor cerebri (PTC), is a neurological disorder that is characterized by increased intracranial pressure (pressure around the brain) in the absence of a tumor or other diseases. It occurs most commonly in obese young women but the cause is unknown. The main symptoms are headache, nausea, and vomiting, as well as pulsatile tinnitus (sounds perceived in the ears, with the sound occurring in the same rhythm as the pulse), double vision and other visual symptoms. If the IIH is untreated, it may lead to papilledema (swelling of the optic disc in the eye) which can progress to vision loss and blindness. Two reviews on the treatment of IIH are Biousse J. Neurol Neurosurg Psychiatry 2012; 83:488-494 and Lueck 2009 issue 4, The Cochrane Collaboration, published by John Wiley and sons. These reviews note that there is no general consensus on how IHH should be managed. Some forms of management are very expensive or have significant complications or both. Several different treatments have been proposed ranging from relatively conservative measures such as diuretic therapy and other drugs such as octreotide, acetrazolamide to more invasive treatments such as optic nerve sheath fenestration, stenting of cerebral venous sinuses, or lumbo-peritoneal shunting; diagnostic lumbar puncture is a valuable intervention beyond its diagnostic importance, and weight management is critical where appropriate.

The use of injected octreotide for this condition has been reported by Panagopoulos et al., Neurology, Neurophysiology and Neuroscience 2007:1; and by Deftereos et al., Cephalalgia, 2011, 31 (16), p. 1679). Upon use of daily injections of octreotide, headache and papilledema subsided and visual disturbances improved in about 90% of patients treated. Treatment continued for 6 months and then tapered off over another 2 months. LAR depot octreotide once monthly had a lower response rate.

The use of oral octreotide instead of the invasive procedures described above (e.g. daily injections, surgery) would be a great benefit to patients.

Vascular headaches, a group that includes migraines, are thought to involve abnormal function of the brain's blood vessels or vascular system. The most common type of vascular headache is migraine headache that is usually characterized by severe pain on one or both sides of the head, nausea and/or vomiting and disturbed vision and intolerance to light. Other kinds of vascular headaches include cluster headaches and headaches caused by a rise in blood pressure. In particular there is no satisfactory prophylactic treatment for these conditions.

Injectable octreotide for cluster headaches and for migraines has been described with varying results. (Matharu et al Ann Neurol 2004 October; 56(4) 488-492; Levy et al Cephalgia 2005 January (1) 48-55. Miller et al Am J Emerg Med 2009 Feb. 27(2) 160-164. The use of oral octreotide is envisaged for treatment and/or for prophylaxis of headaches, in particular vascular headaches.

SUMMARY

The inventors of the present invention have discovered a method of treating acromegaly and other diseases and conditions, including idiopathic intracranial hypertension (IIH) and vascular headaches, in a subject, the method comprising orally administering to the subject at least once daily at least one dosage form comprising an oily suspension comprising octreotide, wherein the octreotide in each dosage form is from about 5 mg to about 35 mg, and wherein the administering occurs at least 1 hour before a meal or least 2 hours after a meal to thereby treat the subject.

Throughout this application, various publications, including United States patents, are referenced by author and year and patents and applications by number. The disclosures of these publications and patents and patent applications in their entireties are hereby incorporated by reference into this application in order to more fully describe the state of the art to which this invention pertains.

Mean='+' symbol, Median=horizontal line within the box, 1st quartile=bottom of box, 3rd quartile=top of box Upper fence=3rd quartile+1.5 IQR, lower fence=1st quartile+1.5 IQR. IQR=interquartile range. Whiskers are drawn to the most extreme points that lie between fences.

Figure 1A:
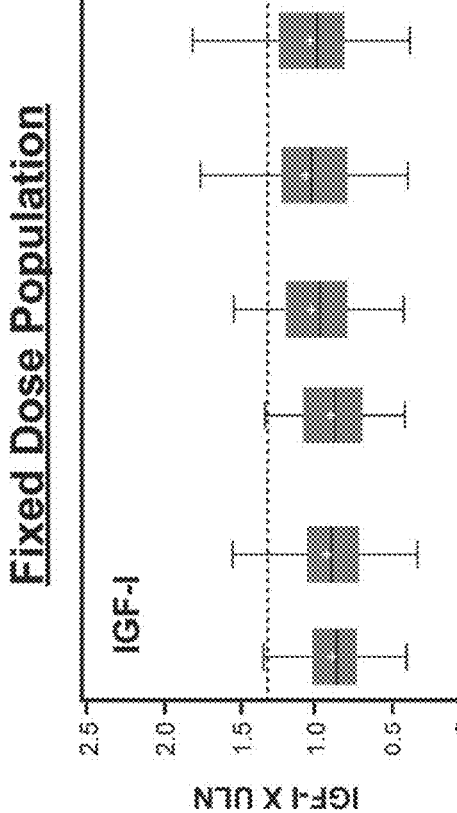
FIGS. 1A-1D: Biochemical control. Boxplot of IGF-I (X ULN) (FIG. 1A, FIG. 1B) and mean integrated GH concentrations (ng/mL) (FIG. 1C, FIG. 1D), by visit in the mITT (FIG. 1A, FIG. 1C) and Fixed Dose (FIG. 1B, FIG. 1D) cohorts. For the mITT population subjects terminating the trial early during the dose escalation (n=41), appear at End of Dose Escalation and patients terminating early during the fixed dose (n=8) appear at End of Core. For the Fixed Dose population, patients terminating the trial early during the fixed dose (n=8), and those not continuing into the extension (n=14), appear at End of Core. End treatment=end of 13 months. Dotted lines=GH and IGF1 screening and primary end-points, respectively.
Figure 1C:
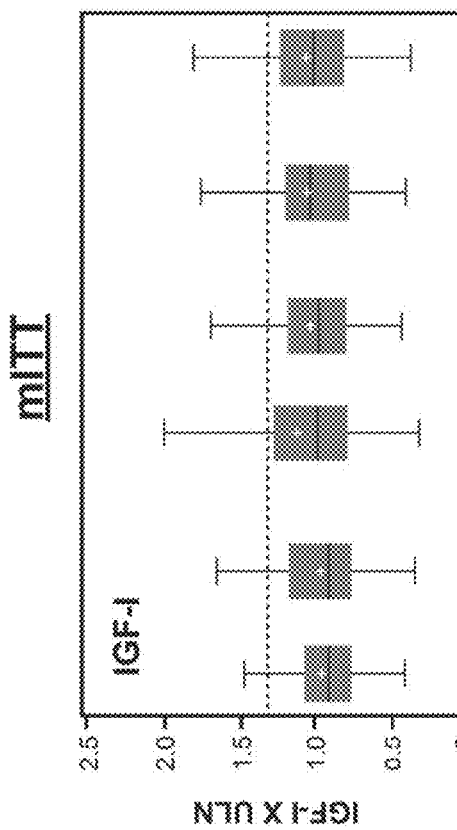
Figure 1B:
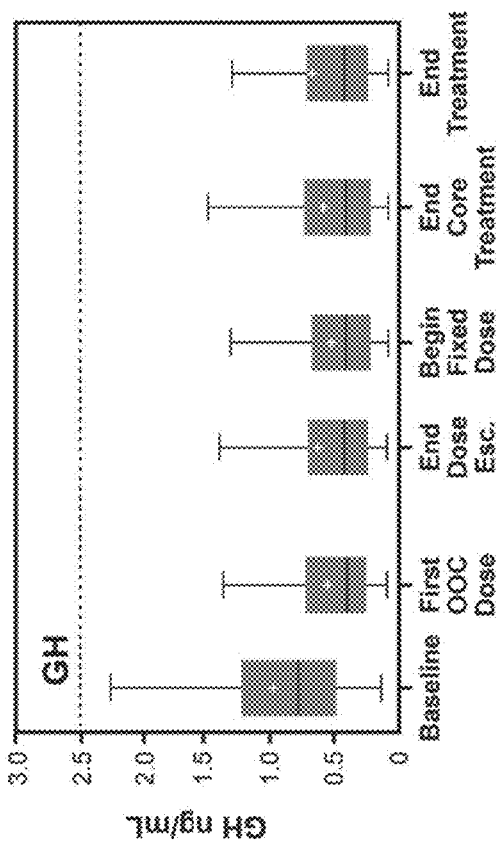
Figure 1D:
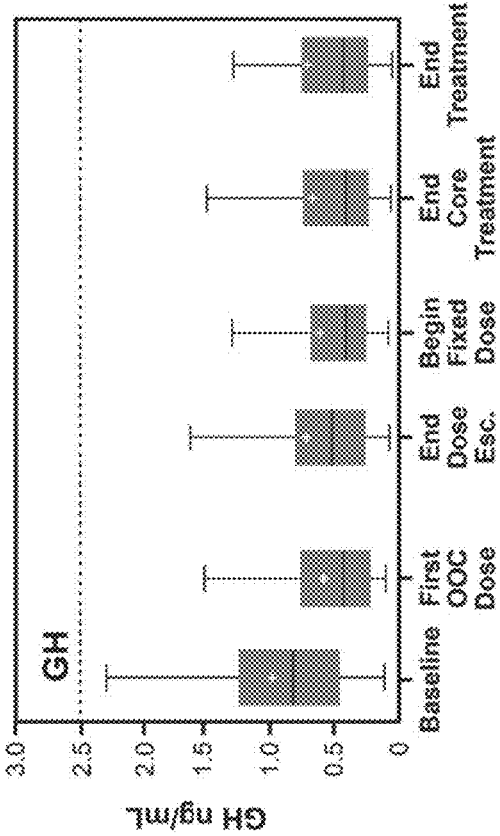
Figure 2:
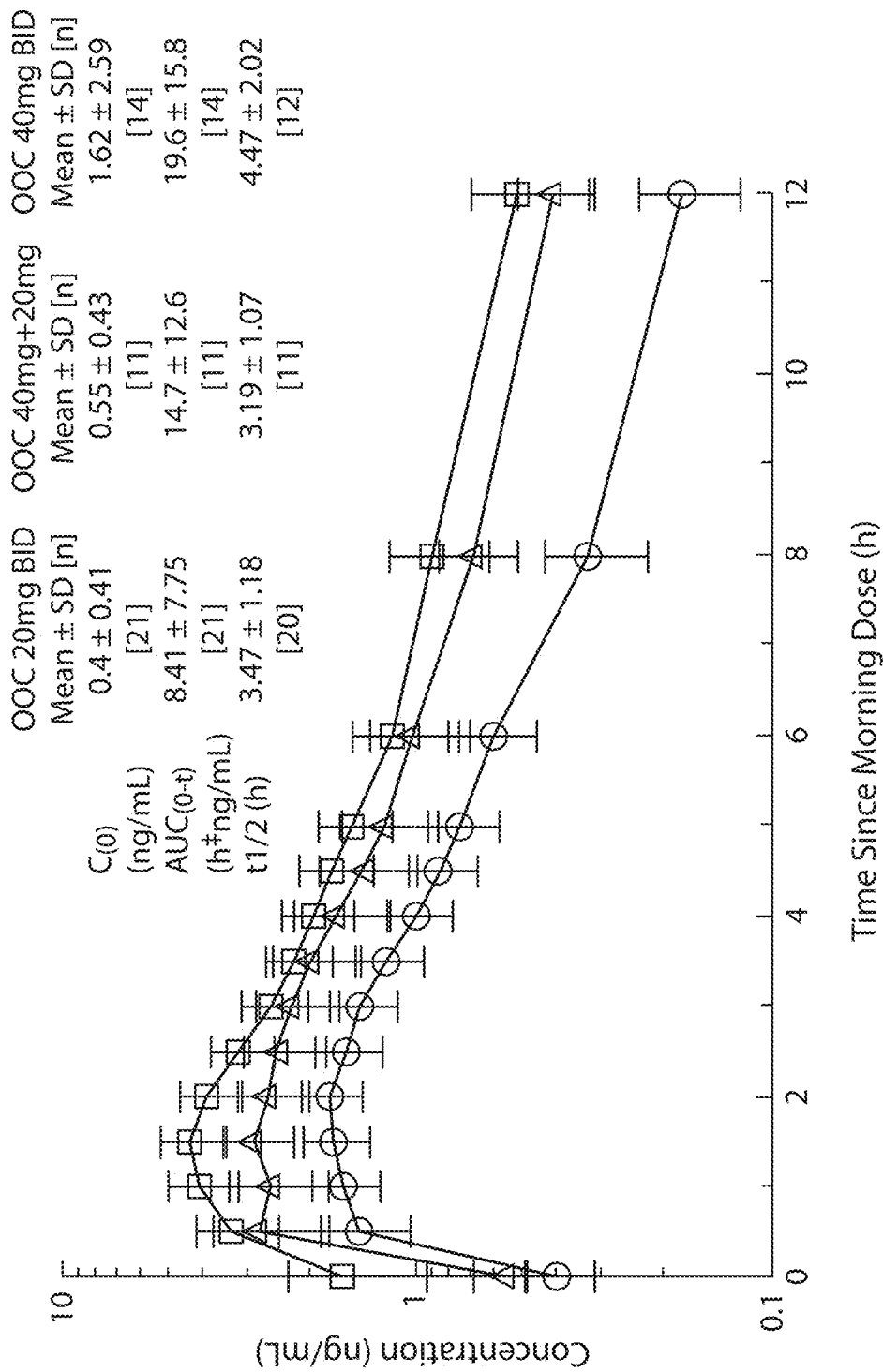

FIG. 2: Pharmacokinetic analysis in 46 subjects undergoing chronic OOC treatment in their second visit of the fix-dose phase. PK was assessed after the morning OOC dose for the 3 tested dosing regimens. A single 20 mg capsule for 20 mg BID regimen (blue circles; n=21), two capsules of 20 mg (40 mg total) of 40 mg+20 mg regimen (red triangles; n=11), and 2 capsules of 20 mg (40 mg total) of 40 mg BID regimen (green rectangles; n=14). The arithmetic mean±standard error plasma octreotide concentrations are presented on a logarithmic scale graph and a summary of PK parameters for octreotide are presented as arithmetic mean+SD (n).

Figure 3:
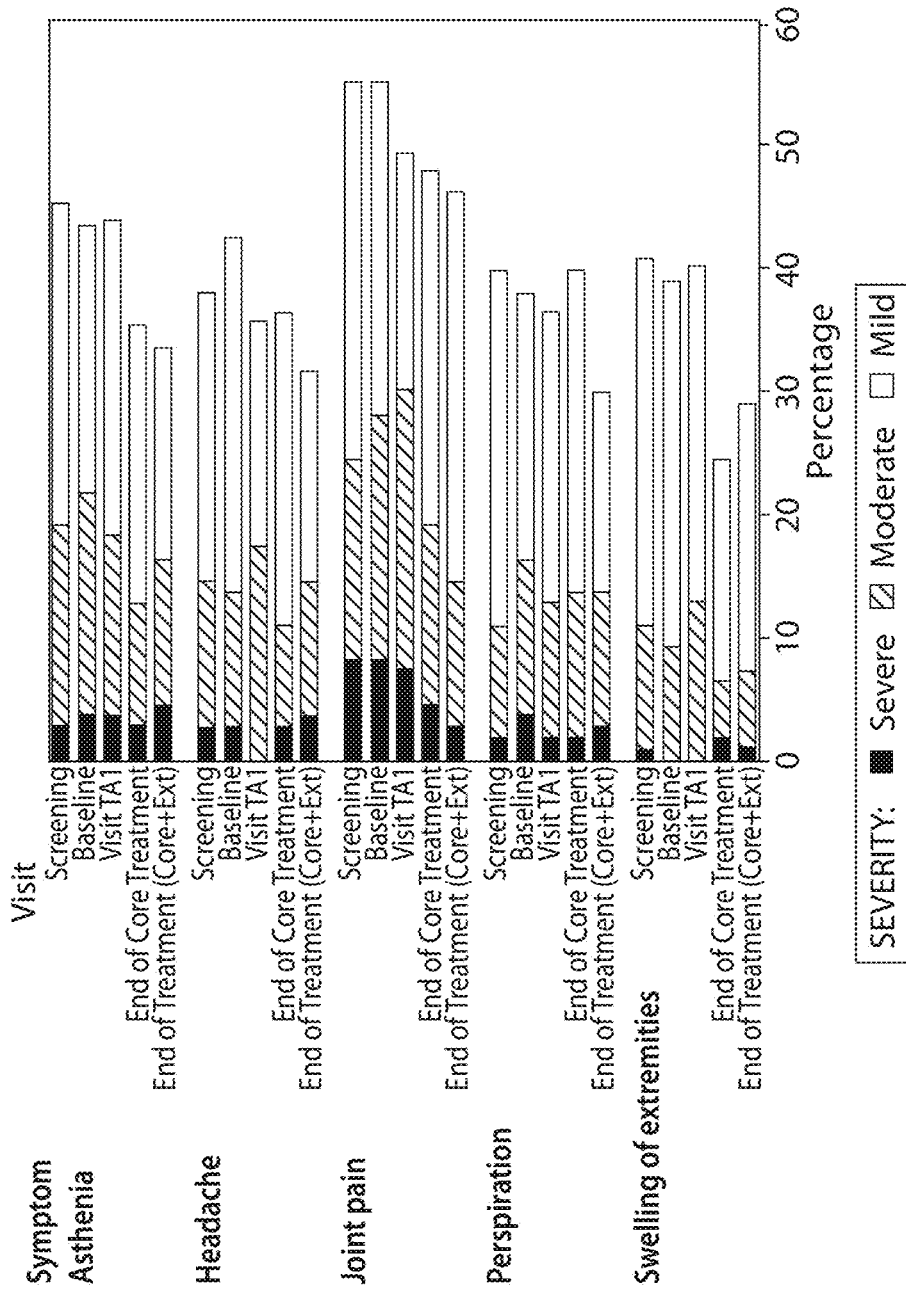

FIG. 3: Proportion of subjects with acromegaly signs and symptoms, by severity in the fixed dose population from screening to end of treatment (including extension). Screening, baseline and TA1 (first OOC administration) depict symptoms on parenteral SRL injections. End of core and end of treatment depict symptoms while on OOC. For this analysis the last observed value on OOC was carried forward to end of treatment.

Figure 4:
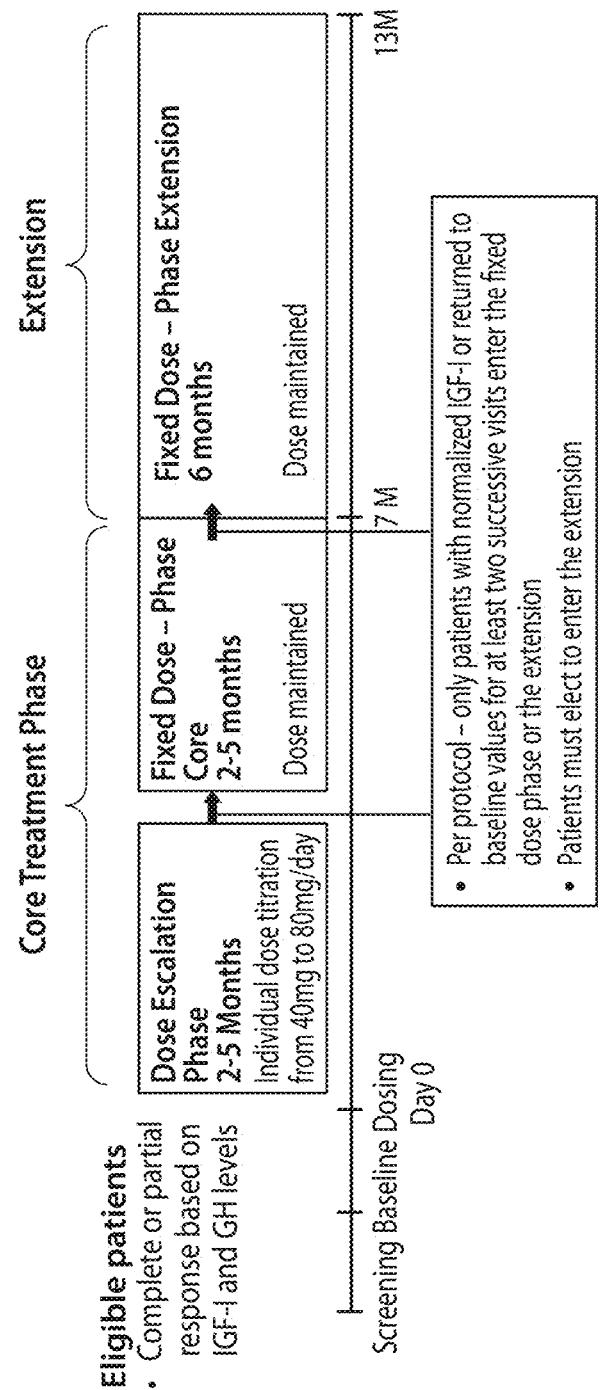

FIG. 4: A flowchart of the study described in the Examples.

DETAILED DESCRIPTION OF THE INVENTION

Treatment of Acromegaly

Acromegaly is caused by a benign (non-cancerous) tumor (an adenoma) within the pituitary gland that secretes excess growth hormone (GH), leading to elevated levels of insulin-like growth factor-1 (IGF-1). This combined effect of elevated GH and IGF-1 levels causes the enlargement of body parts, including the hands, feet and facial features, along with serious morbidities such as cardiovascular, metabolic and respiratory diseases. If exposed to long-term elevated levels of GH and IGF-1, acromegaly patients face a two- to three-fold increased risk of death.

The current treatment of acromegaly is summarized by Giustina et al 2014 (Ref 13) which is hereby incorporated by reference. Biochemical control of the disease, as measured by both GH and IGF-1 levels, is the primary goal of treatment. Other disease management objectives include tumor shrinkage and improvement in clinical signs and symptoms. Thus the main goals of treatment are to control GH and IGF-1 levels and to control acromegaly symptoms.

Various forms of pharmaceutical therapy are used in the art for treatment of acromegaly: most are receptor-based, directed at the pituitary adenoma (the somatostatin receptor ligands—SRLs—octreotide, lanreotide and pasireotide which are all given by injection) and the dopamine agonist cabergoline given orally; and one is directed at decreasing and/or blocking GH effects in the periphery viz., the GH receptor antagonist pegvisomant given by injection. SRLs may be given in slow release formulation or in an immediate release formulation.

Surgery is the primary treatment option if the tumor is resectable. SRLs (injectable octreotide or injectable lanreotide) are the primary first-line treatment after surgery and are the primary treatment option if surgery is not appropriate. Some physicians prescribe dopamine agonists as the primary first-line treatment after surgery. SRLs and dopamine agonists and pegvisomant may also be given before surgery or instead of surgery.

The octreotide capsule described herein is an oral product indicated for long-term maintenance therapy in acromegaly patients; in certain embodiments the patients are those in whom prior treatment with somatostatin analogs (by injection) has been shown to be effective and tolerated. The goal of treatment in acromegaly is to control GH and IGF-1 levels and to lower the GH and IGF-1 levels to as close to normal as possible.

The oral octreotide capsule should preferably be administered with a glass of water on an empty stomach (i.e., at least 1 hour prior to a meal or at least 2 hours after a meal).

Patients currently receiving somatostatin analog therapy by injection can be switched to octreotide capsules with an initial dose of 20 mg BID given orally. Blood levels of IGF-1 and clinical symptoms should be monitored. If IGF-1 is normal and clinical symptoms are controlled or response level (biochemical and symptomatic response) is maintained, maintain oral octreotide capsule dosage at 20 mg BID (ie 40 mg daily). Dosage may be adjusted to 60 mg daily (40 mg morning+20 mg evening) if IGF-1 levels are increased, as determined by the treating physician, or in case of symptomatic exacerbation. Monitoring is continued, while applying the above algorithm for maintaining or increasing the dose up to 40 mg BID is 80 mg daily. The administering throughout occurs at least 2 hours after a meal, or at least 1 hour before a meal.

In another embodiment of the invention, if a capsule containing about 30 mg octreotide is administered, then the above algorithm is used to adjust the dose from 60 mg daily to 90 mg daily and a maximum of 120 mg daily; wherein the administering occurs at least 2 hours after a meal, or at least 1 hour before a meal. In another embodiment, if a capsule containing about 30 mg octreotide is administered, then the above algorithm is used to adjust the dose from 30 mg daily (only one capsule taken) to 60 mg daily to 90 mg daily and a maximum of 120 mg daily; wherein the administering occurs at least 2 hours after a meal, or at least 1 hour before a meal.

In a further embodiment of the invention, if a capsule containing less than 20 mg octreotide is administered e.g. 10 mg, then the above algorithm is adjusted concomitantly. For example in an embodiment of the invention, if a capsule containing about 10 mg octreotide is administered, then the above algorithm is used to adjust the dose from 20 mg daily to 30 mg daily and a maximum of 60 mg daily as needed; wherein the administering occurs at least 2 hours after a meal, or at least 1 hour before a meal.

The invention may be used in the treatment of naïve patients or patients already treated with parenteral injections.

Patients who are not adequately controlled following dose titration can return to therapy by injections at any time. Proton pump inhibitors (PPIs), H2-receptor antagonists, and antacids may lead to a higher dosing requirement of oral octreotide to achieve therapeutic levels.

One embodiment of the invention is a method of treating acromegaly in a subject, the method comprising orally administering to the subject at least once daily at least one dosage form comprising an oily suspension comprising octreotide, wherein the octreotide in each dosage form is from about 5 mg to about 35 mg (e.g. 5, 10, 15, 20, 25, 30 or 35 mg), and wherein the administering occurs at least 1 hour before a meal or at least 2 hours after a meal, to thereby treat the subject. Another embodiment of the invention is a method of treating acromegaly in a subject, the method comprising orally administering to the subject at least once daily at least one dosage form comprising an oily suspension comprising octreotide, wherein the octreotide in each dosage form is from about 18 mg to about 22 mg, and wherein the administering occurs at least 1 hour before a meal or at least 2 hours after a meal to thereby treat the subject.

A dosage form is essentially a pharmaceutical product in the form in which it is marketed for use, typically involving a mixture of active drug components and nondrug components (excipients), along with other non-reusable material that may not be considered either ingredient or packaging (such as a capsule shell, for example).

The oily suspension as used herein comprises an admixture of a hydrophobic medium (lipophilic fraction) and a solid form (hydrophilic fraction) wherein the solid form comprises a octreotide and at least one salt of a medium chain fatty acid, and wherein the medium chain fatty acid salt is present in the composition at an amount of 10% or more by weight such as 11%-15%, or 11%, 12%, 13%, 14%, 15% or more by weight.

Oral formulations of octreotide, comprising the oily suspension, have been described and claimed, for example in co-assigned U.S. Pat. No. 8,329,198 which is hereby incorporated by reference; see for example claims 1-26.

In a particular embodiment of the method of the invention the oily suspension is formulated into a capsule, which may be enterically coated. In another embodiment of the method of the invention the capsule consists of an oily suspension. In another embodiment of the method of the invention the subject is dosed every 8-16 hours (e.g., every 12 hours). In another embodiment of the method of the invention one administration takes place at least 6, 8, 10 or 12 hours before a second administration. In a preferred embodiment the subject is a human.

For clarity, the twice daily administration comprises a first administration and a second administration. In a further embodiment a first administration includes one or two dosage forms and a second administration includes one or two dosage forms, and more particularly the first administration includes one dosage form and the second administration includes one dosage form, or the first administration includes two dosage forms and the second administration includes one dosage form, or the first administration includes two dosage forms and the second administration includes two dosage forms. In embodiments of the invention the first administration is in the morning (normally 5 am to noon) and the second administration is in the evening (normally 5 pm to midnight). All the administering occurs at least 1 hour before a meal or at least 2 hours after a meal.

Particular embodiments of the invention are as follows: one dosage form is administered twice daily; two dosage forms are administered once a day and one dosage form is administered once a day; and two dosage forms are administered twice daily. Other embodiments of the invention are as follows: one dosage form is administered once a day; two dosage forms are administered once a day; three or more dosage forms are administered once a day; and two or more dosage forms (e.g. three dosage forms) are administered twice a day. All the administering occurs at least 1 hour before a meal or at least 2 hours after a meal.

In some embodiments of the invention, the administration may be self-administration; in other embodiments of the invention or a caregiver or health professional may administer the dosage form.

In certain embodiments of the invention each dosage form comprises from about 19 to about 21 mg of octreotide and in a particular embodiment of the invention each dosage form comprises 20 mg of octreotide which is about 3% w/w octreotide or 3.3% w/w octreotide. In certain embodiments of the invention the total amount of octreotide administered per day is from about 36 to about 44 mg (e.g., from about 38 to about 42 mg, or 40 mg). In certain embodiments of the invention the total amount of octreotide administered per day is from about 54 to about 66 mg (e.g., from about 57 to about 63 mg, or 60 mg). In certain embodiments of the invention the total amount of octreotide administered per day is from about 72 to about 88 mg (e.g., from about 76 to about 84 mg, or 80 mg). In certain embodiments of the invention the total amount of octreotide administered per day is from about 90 to about 110 mg (e.g., from about 95 to about 105 mg, or 100 mg). All the administering occurs at least 1 hour before a meal or at least 2 hours after a meal.

In certain embodiments of the invention each dosage form comprises from about 27 to about 33 mg of octreotide and in a particular embodiment of the invention each dosage form comprises 30 mg of octreotide which is about 5% w/w octreotide or 4.96% w/w octreotide. This may be administered as one, two, three or four capsules per day, wherein administering occurs at least 1 hour before a meal or at least 2 hours after a meal.

In another embodiments of the invention each dosage form comprises less than 20 mg octreotide and in a particular embodiment of the invention each dosage form comprises about 10 mg. This may be administered as one, two, three or four capsules per day, wherein administering occurs at least 1 hour before a meal or at least 2 hours after a meal.

In further embodiments, the method of the invention occurs over a duration of at least 7 months, occurs over a duration of at least 13 months and over a duration of greater than 13 months. In a particular embodiment the method of treatment is for long-term maintenance therapy. Long-term maintenance therapy in a subject suffering from acromegaly continues as long as the subject is suffering from acromegaly and the IGF-1 levels are maintained at equal or less than 1.3 times the upper limit of the age-adjusted normal range (ULN). Thus the duration may be unlimited. In particular embodiments the long-term maintenance therapy may be for at least one, two, three, four or five years. In a particular embodiment upon administration of octreotide, an in vivo amount of growth hormone integrated over 2 hours is obtained which is equal or less than 2.5 ng/mL or equal or less than 1.0 ng/mL.

In further embodiments, upon administration of octreotide, an in vivo concentration of IGF-I is obtained of equal or less than 1.3 times the upper limit of the age-adjusted normal range (ULN), or equal or less than 1.0 or 1.1 or 1.2 or 1.4 or 1.5 or 1.6 times the upper limit of the age-adjusted normal range (ULN).

In certain embodiments, an in vivo mean peak plasma concentration upon administration of octreotide of about 3.5+/−0.5 ng/mL is achieved. In certain embodiments an in vivo mean area under the curve upon administration of octreotide is about 15+/−4 hxng/mL is obtained.

In particular embodiments of the method of the invention the subject has had prior treatment for acromegaly, and the prior treatment for acromegaly was surgical and/or medicinal; in certain embodiments the medicinal treatment was a somatostatin analog (=somatostatin receptor ligand) e.g. injectable octreotide or injectable lanreotide or injectable pasireotide and/or a dopamine agonist e.g. cabergoline and/or a GH receptor antagonist e.g. pegvisomant.

In particular embodiments the prior treatment of the subject with a somatostatin analog has been shown to be effective and tolerated.

In particular embodiments the prior treatment of the subject produced an IGF-1 level in the subject of equal or less than 1.3 times upper limit of normal (ULN), and/or prior treatment of the subject produced 2-hour integrated growth hormone (GH) of less than 2.5 ng/mL or less than 1.0 ng/mL Preferably the oral octreotide capsule should be administered on an empty stomach (i.e., at least 1 hour prior to a meal or at least 2 hours after a meal. In particular embodiments of all inventions describes herein, a meal comprises 100-1000 calories, or 300-600 calories which may be a high-fat meal or a high calorie meal and may comprise carbohydrates and/or fat and or protein e.g. 100, 200, 300, 400 calories or 500-1000 calories or 700-800 calories.

The invention also contemplates titrating a patient suffering from acromegaly to determine the effective dose of octreotide. Such an embodiment of the invention relates to a method of titrating a patient having acromegaly, the method comprising orally administering to the subject at least once daily (e.g. twice daily) at least one dosage form comprising an oily suspension comprising octreotide, wherein the octreotide in each dosage form is from about 18 mg to about 22 mg, wherein the total amount of octreotide administered per day is from about 36 to about 44 mg; and subsequent to the administration, evaluating an IGF-1 level (and/or a GH level) in a subject and comparing the level to a reference standard; wherein if the IGF-1 level (and/or the GH level) is above the reference standard, increasing the total amount of octreotide administered per day to from about 54 to about 66 mg; wherein the administering occurs at least 2 hours after a meal, or at least 1 hour before a meal.

Another such embodiment of the invention relates to a method of titrating a patient having acromegaly, the method comprising orally administering to the subject at least once daily (e.g. twice daily) at least one dosage form comprising an oily suspension comprising octreotide, wherein the octreotide in each dosage form is from about 18 mg to about 22 mg, wherein the total amount of octreotide administered per day is from about 54 to about 66 mg; and subsequent to the administration, evaluating an IGF-1 level (and/or a GH level) in a subject and comparing the level to a reference standard; wherein if the IGF-1 level (and/or the GH level) is above the reference standard, increasing the total amount of octreotide administered per day to from about 72 to about 88 mg; wherein the administering occurs at least 2 hours after a meal or at least 1 hour before a meal.

In one embodiment of the invention, if a capsule containing about 30 mg octreotide is administered, then the above algorithm is used to adjust the dose from 60 mg daily to 90 mg daily and a maximum of 120 mg daily; wherein the administering occurs at least 2 hours after a meal, or at least 1 hour before a meal. In another embodiment, if a capsule containing about 30 mg octreotide is administered, then the above algorithm is used to adjust the dose from 30 mg daily (only one capsule taken) to 60 mg daily (two capsules) to 90 mg daily (three capsules) and a maximum of 120 mg daily (four capsules); wherein the administering occurs at least 2 hours after a meal, or at least 1 hour before a meal.

In a further embodiment of the invention, if a capsule containing less than 20 mg octreotide is administered e.g. 10 mg, then the above algorithm is adjusted concomitantly.

In further embodiments of the titrating invention the oily suspension is formulated into a capsule; the capsule is enterically coated; the oral administration is twice daily comprising a first and second administration; the subject is dosed every 8-16 hours (e.g., every 12 hours); one administration takes place at least 6, 8, 10 or 12 hours before a second administration; and the subject is a human. In a further embodiment of the titrating invention the first administration prior to evaluation includes one or two dosage forms and the second administration includes one or two dosage forms. In a further embodiment of the titrating invention, the first daily administration prior to evaluation includes one dosage form and the second daily administration prior to evaluation includes one dosage form. In a further embodiment of the titrating invention the first daily administration prior to evaluation includes two dosage forms and the second daily administration prior to evaluation includes one dosage form. In a further embodiment of the titrating invention the first daily administration after evaluation includes two dosage forms and the second daily administration after evaluation includes two dosage forms. In a further embodiment of the invention one dosage form is administered once a day and two dosage forms are administered once a day, prior to evaluation. In a further embodiment of the invention two dosage forms are administered twice daily after evaluation. Administering occurs at least 2 hours after a meal, or at least 1 hour before a meal.

In a further embodiment of the invention each dosage form comprises from about 19 to about 21 mg of octreotide, more particularly 20 mg of octreotide which is about 3% w/w octreotide. In a further embodiment of the invention the total amount of octreotide administered per day prior to evaluation is from about 36 to about 44 mg (e.g., from about 38 to about 42 mg, or 40 mg). In a further embodiment of the invention the total amount of octreotide administered per day prior to evaluation is from about 54 to about 66 mg (e.g., from about 57 to about 63 mg, or 60 mg).

In a further embodiment of the invention the total amount of octreotide administered per day subsequent to evaluation is from about 54 to about 66 mg (e.g., from about 57 to about 63 mg, or 60 mg). In a further embodiment of the invention the total amount of octreotide administered per day subsequent to evaluation is from about 72 to about 88 mg (e.g., from about 76 to about 84 mg, or 80 mg). In a further embodiment of the invention the evaluation takes place at least two months from start of therapy (i.e. from start of administration of the dosage forms), 2-5 months from start of therapy or after 5 months from start of therapy (e.g. after 5, 6, 7 or 8 months or more from start of therapy).

In a specific embodiment of the invention the blood levels of IGF-1 and clinical symptoms are monitored when oral octreotide capsule dosage at 40 mg (20 mg BID), and if IGF-1 is normal and clinical symptoms are controlled or response level (biochemical and symptomatic response) is maintained, then oral octreotide capsule dosage is continued at 40 mg (20 mg BID). In a further specific embodiment of the invention the blood levels of IGF-1 and clinical symptoms are further monitored when oral octreotide capsule dosage is at 40 mg, and if IGF-1 is not normal and clinical symptoms are not controlled or response level (biochemical and symptomatic response) is not maintained, then oral octreotide capsule dosage is increased to 60 mg daily (40 mg morning+20 mg evening). In a further specific embodiment of the invention the blood levels of IGF-1 and clinical symptoms are further monitored when oral octreotide capsule dosage is at 60 mg, and if IGF-1 is normal and clinical symptoms are controlled or response level (biochemical and symptomatic response) is maintained, then oral octreotide capsule dosage is continued at 60 mg daily. In a further specific embodiment of the invention the blood levels of IGF-1 and clinical symptoms are further monitored when oral octreotide capsule dosage is at 60 mg, and if IGF-1 is not normal and clinical symptoms are not controlled or response level (biochemical and symptomatic response) is not maintained, then oral octreotide capsule dosage is increased to 80 mg (40 mg morning+40 mg evening)

In a further embodiment of the invention the reference standard is an in vivo amount of growth hormone integrated over 2 hours is obtained which is equal or less than 2.5 ng/mL (for example equal or less than 1.0 ng/mL). In a further embodiment of the invention the reference standard is an in vivo concentration of IGF-I is obtained of equal or less than 1.3 times the upper limit of the age-adjusted normal range (ULN). In a further embodiment of the invention an in vivo mean peak plasma concentration upon administration of octreotide after evaluation is about 3.5+/−0.5 ng/mL. In a further embodiment of the invention an in vivo mean area under the curve upon administration of octreotide after evaluation is about 15+/−4 h×ng/mL. In a further embodiment of the titrating invention the subject has had prior treatment for acromegaly which was surgical and/or pharmaceutical e.g. the pharmaceutical treatment was a somatostatin receptor ligand e.g. octreotide or lanreotide and was administered by injection. In a further embodiment of the titrating invention prior treatment of the subject with a somatostatin analog has been shown to be effective and tolerated. In a further embodiment of the invention the prior pharmaceutical treatment was pegvisomant or a dopamine agonist e.g. cabergoline.

In a further embodiment of the invention, prior treatment of the subject produced an IGF-1 level in the subject of equal or less than 1.0 to 1.5 times upper limit of normal (ULN) e.g. equal or less than 1.3 times upper limit of normal (ULN). In a further embodiment of the invention prior treatment of the subject produced 2-hour integrated growth hormone (GH) of less than 2.5 ng/mL e.g. less than 1.0 ng/mL.

A further embodiment of the invention is a method of predicting subsequent response to oral octreotide capsules in a patient receiving injectable treatment. Thus an embodiment of the invention is a method of predicting subsequent response to oral octreotide capsules comprising the oily suspension in a patient suffering from acromegaly, the method comprising measuring the degree of baseline control on injectable SRLs; and thereby determining if the patient is likely to respond to the oral octreotide capsules. In an embodiment of the invention the desired baseline control is IGF-I≤1ULN and GH<2.5 ng/mL when the patient is maintained on low to mid doses of injectable SRLs (octreotide<30 mg or lanreotide<120 mg).

Treatment of Idiopathic Intracranial Hypertension (IIH)

Another embodiment of the invention is a method of treating idiopathic intracranial hypertension (IIH) in a subject, the method comprising orally administering to the subject at least once daily at least one dosage form comprising an oily suspension comprising octreotide, wherein the octreotide in each dosage form is from about 5 mg to about 35 mg (e.g. 5, 10, 15, 20, 25, 30 or 35 mg), and wherein the administering occurs at least 1 hour before a meal or at least 2 hours after a meal, to thereby treat the subject. In a particular embodiment the octreotide in each dosage form is from about 18 mg to about 22 mg. In another embodiment the octreotide in each dosage form is from about 27 mg to about 33 mg e.g. about 30 mg.

The oily suspension as used herein comprises an admixture of a hydrophobic medium (lipophilic fraction) and a solid form (hydrophilic fraction) wherein the solid form comprises a octreotide and at least one salt of a medium chain fatty acid, and wherein the medium chain fatty acid salt is present in the composition at an amount of 10% or more by weight such as 11%-15%, or 11%, 12%, 13%, 14%, 15% or more by weight. The oily suspension of the invention is as described herein. In a particular embodiment of the method of the invention the oily suspension is formulated into a capsule, which may be enterically coated. In another embodiment of the method of the invention the capsule consists of an oily suspension. In another embodiment of the method of the invention the subject is dosed every 8-16 hours (e.g., every 12 hours). In another embodiment of the method of the invention one administration takes place at least 6, 8, 10 or 12 hours before a second administration. In a preferred embodiment the subject is a human.

For clarity, the twice daily administration comprises a first administration and a second administration. In a further embodiment a first administration includes one or two dosage forms and a second administration includes one or two dosage forms, and more particularly the first administration includes one dosage form and the second administration includes one dosage form or the first administration includes two dosage forms and the second administration includes one dosage form or the first administration includes two dosage forms and the second administration includes two dosage forms. In embodiments of the invention the first administration is in the morning (normally 5 am to noon) and the second administration is in the evening (normally 5 pm to midnight).

Particular embodiments of the invention are as follows: one dosage form is administered twice daily; two dosage forms are administered once a day and one dosage form is administered once a day; and two dosage forms are administered twice daily. Other embodiments of the invention are as follows: one dosage form is administered once a day; two dosage forms are administered once a day; three or more dosage forms are administered once a day; and two or more dosage forms (e.g. three dosage forms) are administered twice a day.

In some embodiments of the invention, the administration may be self-administration; in other embodiments of the invention or a caregiver or health professional may administer the dosage form.

In certain embodiments of the invention each dosage form comprises from about 19 to about 21 mg of octreotide and in a particular embodiment of the invention each dosage form comprises 20 mg of octreotide which is about 3% w/w octreotide or 3.3% w/w octreotide. In certain embodiments of the invention the total amount of octreotide administered per day is from about 36 to about 44 mg (e.g., from about 38 to about 42 mg, or 40 mg). In certain embodiments of the invention the total amount of octreotide administered per day is from about 54 to about 66 mg (e.g., from about 57 to about 63 mg, or 60 mg). In certain embodiments of the invention the total amount of octreotide administered per day is from about 72 to about 88 mg (e.g., from about 76 to about 84 mg, or 80 mg). In certain embodiments of the invention each dosage form comprises from about 5 to about 35 mg of octreotide and in a particular embodiment of the invention each dosage form comprises about 5 or 10 or 15 or 20 or 25 or 30 or 35 mg of octreotide.

In further embodiments of the invention the method occurs over a duration of at least 7 months or more. In further embodiments of the invention the method can be tapered off after a few months e.g. over 2 months or more. In further embodiments of the invention the method can be tapered off after about 2, 3, 4, 5, 6, 7, 8, 9, or 10 months or more.

In further embodiments of the invention the capsule comprises 20 mg octreotide which is about 3% w/w octreotide. In further embodiments of the invention the capsule comprises about 10 mg octreotide or about 30 mg octreotide.

In further embodiments of the invention the oily suspension comprises an admixture of a hydrophobic medium (lipophilic fraction) and a solid form (hydrophilic fraction) wherein the solid form comprises a octreotide and at least one salt of a medium chain fatty acid, and wherein the medium chain fatty acid salt is present in the composition at an amount of 10% or more by weight (e.g. at an amount of 11%-16% or more such as 11%, 12%, 13%, 14%, 15%, 16% by weight).

In particular embodiments of the invention upon administration of octreotide, headache is relieved. In particular embodiments of the invention upon administration of octreotide, visual disturbances are reduced. In particular embodiments of the invention upon administration of octreotide, papilledema subside. In particular embodiments of the invention upon administration of octreotide, the CSF opening pressure is reduced e.g. to to 8-23 cm $H_2O$ preferably 10-18 cm $H_2O$.

In another embodiment another SRL (e.g., lanreotide) may be used orally to treat IIH. Thus an embodiment of the invention is a method of treating idiopathic intracranial hypertension (IIH) in a subject, the method comprising orally administering to the subject at least once daily at least one dosage form containing lanreotide to thereby treat the subject. In a specific embodiment the administering occurs at least 1 hour before a meal or at least 2 hours after a meal.

The invention also contemplates titrating a patient suffering from IIH to determine the effective dose of octreotide.

This embodiment comprises titrating a patient having idiopathic intracranial hypertension (IIH), the method comprising orally administering to the subject at least once daily at least one dosage form comprising an oily suspension comprising octreotide, wherein the octreotide in each dosage form is from about 18 mg to about 22 mg, wherein the total amount of octreotide administered per day is from about 36 to about 44 mg; and subsequent to the administration, evaluating an IIH symptom in a subject and comparing the level to a reference standard; wherein if the IIH symptom is above the reference standard, increasing the total amount of octreotide administered per day to from about 54 to about 66 mg; wherein the administering occurs at least 1 hour before a meal or at least 2 hours after a meal.

In one embodiment of the invention, if a capsule containing about 30 mg octreotide is administered, then the above algorithm is used to adjust the dose from 60 mg daily to 90 mg daily and a maximum of 120 mg daily; wherein the administering occurs at least 2 hours after a meal, or at least 1 hour before a meal. In another embodiment, if a capsule containing about 30 mg octreotide is administered, then the above algorithm is used to adjust the dose from 30 mg daily (only one capsule taken) to 60 mg daily to 90 mg daily and a maximum of 120 mg daily; wherein the administering occurs at least 2 hours after a meal, or at least 1 hour before a meal.

In a further embodiment of the invention, if a capsule containing less than 20 mg octreotide is administered e.g. 10 mg, then the above algorithm is adjusted concomitantly.

This embodiment also comprises a method of titrating a patient having idiopathic intracranial hypertension (IIH), the method comprising orally administering to the subject at least once daily at least one dosage form comprising an oily suspension comprising octreotide, wherein the octreotide in each dosage form is from about 18 mg to about 22 mg, wherein the total amount of octreotide administered per day is from about 54 to about 66 mg; and subsequent to the administration, evaluating an IIH symptom in a subject and comparing the level to a normal reference standard; wherein if symptom is above the reference standard, increasing the total amount of octreotide administered per day to from about 72 to about 88 mg; wherein the administering occurs at least 2 hours after a meal or at least 1 hour before a meal.

In further embodiments of the titrating invention the oily suspension is formulated into a capsule; the capsule is enterically coated; the oral administration is twice daily comprising a first and second administration; the subject is dosed every 8-16 hours (e.g., every 12 hours); one administration takes place at least 6, 8, 10 or 12 hours before a second administration; and the subject is a human. In a further embodiment of the titrating invention the first administration prior to evaluation includes one or two dosage forms and the second administration includes one or two dosage forms. In a further embodiment of the titrating invention, the first daily administration prior to evaluation includes one dosage form and the second daily administration prior to evaluation includes one dosage form. In a further embodiment of the titrating invention the first daily administration prior to evaluation includes two dosage forms and the second daily administration prior to evaluation includes one dosage form. In a further embodiment of the titrating invention the first daily administration after evaluation includes two dosage forms and the second daily administration after evaluation includes two dosage forms. In a further embodiment of the invention one dosage form is administered once a day and two dosage forms are administered once a day, prior to evaluation. In a further embodiment of the invention two dosage forms are administered twice daily after evaluation.

In a further embodiment of the invention each dosage form comprises from about 19 to about 21 mg of octreotide, more particularly 20 mg of octreotide which is about 3% w/w octreotide. In a further embodiment of the invention the total amount of octreotide administered per day prior to evaluation is from about 36 to about 44 mg (e.g., from about 38 to about 42 mg, or 40 mg). In a further embodiment of the invention the total amount of octreotide administered per day prior to evaluation is from about 54 to about 66 mg (e.g., from about 57 to about 63 mg, or 60 mg).

In a further embodiment of the invention the total amount of octreotide administered per day subsequent to evaluation is from about 54 to about 66 mg (e.g., from about 57 to about 63 mg, or 60 mg). In a further embodiment of the invention the total amount of octreotide administered per day subsequent to evaluation is from about 72 to about 88 mg (e.g., from about 76 to about 84 mg, or 80 mg). In a further embodiment of the invention the evaluation takes place about one week or one month from start of therapy (i.e. from start of administration of the dosage forms), 2-5 months from start of therapy or after 5 months from start of therapy (e.g. after 5, 6, 7 or 8 months or more from start of therapy).

In a further embodiment of the titrating invention, the oily suspension comprises an admixture of a hydrophobic medium (lipophilic fraction) and a solid form (hydrophilic fraction) wherein the solid form comprises a octreotide and at least one salt of a medium chain fatty acid, and wherein the medium chain fatty acid salt is present in the composition at an amount of 10% or more by weight (e.g. at an amount of 11%-16% or more such as 11%, 12%, 15%, 16% by weight). In a particular embodiment the capsule comprises 20 mg octreotide which is about 3% w/w octreotide. In another particular embodiment the capsule comprises about 10 mg octreotide or about 30 mg octreotide.

In a further embodiment of the titrating invention the IIH symptom is one or more of headache, papilledema and visual disturbance. In a further embodiment of the titrating invention the reference standard is the normal for a healthy person not suffering from IIH e.g. no headache, no papilledema and no visual disturbance.

Treatment of Vascular Headaches

A further embodiment of the invention is a method of treating or prophylaxis of headaches in particular vascular headaches, which are thought to involve abnormal function of the brain's blood vessels or vascular system. The most common type of vascular headache is migraine headache. Other kinds of vascular headaches include cluster headaches and headaches caused by a rise in blood pressure.

Migraines typically present with self-limited, recurrent severe headache associated with autonomic symptoms.

Cluster headache is a neurological disorder characterized by recurrent, severe headaches on one side of the head, typically around the eye. There are often accompanying autonomic symptoms during the headache such as eye watering, nasal congestion and swelling around the eye, typically confined to the side of the head with the pain.

The use of oral octreotide is envisaged to treat headaches in particular vascular headaches including migraines and cluster headaches. Thus an embodiment of the invention is a method of treating headaches in particular vascular headaches including migraines and cluster headaches in a subject, the method comprising orally administering to the subject at least once daily at least one dosage form containing octreotide to thereby treat the subject. In a specific embodiment, the administering occurs at least 1 hour before a meal or at least 2 hours after a meal. The treatment may comprise aborting a headache or prophylactic treatment wherein oral octreotide is taken on an ongoing prophylactic basis.

In another embodiment another SRL (e.g., lanreotide) may be used orally to treat headaches in particular vascular headaches including migraines and cluster headaches. Thus an embodiment of the invention is a method of treating headaches in particular vascular headaches including migraines and cluster headaches in a subject, the method comprising orally administering to the subject at least once daily at least one dosage form containing lanreotide to thereby treat the subject. In a specific embodiment the administering occurs at least 1 hour before a meal or at least 2 hours after a meal. The treatment may comprise aborting a headache or prophylactic treatment wherein oral lanreotide is taken on an ongoing prophylactic basis.

A particular embodiment of the invention is a method of prophylactically treating or aborting headache in a subject, the method comprising orally administering to the subject at least once daily at least one dosage form comprising an oily suspension comprising octreotide, wherein the octreotide in each dosage form is from about 5 mg to about 35 mg (e.g. 5, 10, 15, 20, 25, 30 or 35 mg), and wherein the administering occurs at least 1 hour before a meal or at least 2 hours after a meal, to thereby treat the subject. In particular embodiments of the invention the headache may be a vascular headache, which may be a migraine or a cluster headache or the headache may be caused by IIH.

In a particular embodiment of the invention the oily suspension is formulated into a capsule, and the capsule may be enterically coated. In particular embodiments of the invention the oral administration is twice daily (e.g., administering one or two dosage forms at each administration), comprising a first and second administration; the subject is dosed every 8-16 hours (e.g., every 12 hours); one administration takes place at least 6, 8, 10 or 12 hours before a second administration; the subject is a human.

In particular embodiments of the invention the first administration includes one or two dosage forms and the second administration includes one or two dosage forms. In further embodiments of the invention the first administration includes one dosage form and the second administration includes one dosage form or the first administration includes two dosage forms and the second administration includes one dosage form. or the first administration includes two dosage forms and the second administration includes two dosage forms.

In further embodiments of the invention one dosage form is administered twice a day or two dosage forms are administered twice a day or one dosage form is administered once a day and two dosage forms are administered once a day.

In particular embodiments of the invention each dosage form comprises from about 19 to about 21 mg of octreotide or each dosage form comprises 20 mg of octreotide. In another embodiment of the invention each dosage form comprises from about 27 to about 33 mg of octreotide or each dosage form comprises 30 mg of octreotide In particular embodiments of the invention the total amount of octreotide administered per day is from about 36 to about 44 mg (e.g., from about 38 to about 42 mg, or 40 mg); or the total amount of octreotide administered per day is from about 54 to about 66 mg (e.g., from about 57 to about 63 mg, or 60 mg); or the total amount of octreotide administered per day is from about 72 to about 88 mg (e.g., from about 76 to about 84 mg, or 80 mg).

If a capsule containing about 30 mg octreotide is administered, then the dose is 30 mg daily or 60 mg daily or 90 mg daily and a maximum of 120 mg daily; wherein the administering occurs at least 2 hours after a meal, or at least 1 hour before a meal.

In certain embodiments of the invention each dosage form comprises from about 5 to about 35 mg of octreotide and in a particular embodiment of the invention each dosage form comprises about 5 or 10 or 15 or 20 or 25 or 30 or 35 mg of octreotide.

In particular embodiments of the invention the method occurs over a duration of at least 7 months, for prophylactic treatment and in particular embodiments of the invention the method can be tapered off after a few months.

In particular embodiments of the invention the method the method occurs over a duration of about a day, or about one to two days or more for abortive treatment. In particular embodiments of the invention the capsule comprises 20 mg octreotide which is about 3% w/w octreotide. In other embodiments of the invention the capsule comprises 10 mg octreotide or 30 mg octreotide.

In particular embodiments of the invention the oily suspension comprises an admixture of a hydrophobic medium (lipophilic fraction) and a solid form (hydrophilic fraction) wherein the solid form comprises a octreotide and at least one salt of a medium chain fatty acid, and wherein the medium chain fatty acid salt is present in the composition at an amount of 10% or more by weight (e.g. at an amount of 11%-16% or more such as 11%, 12%, 15%, 16% by weight).

In particular embodiments of the invention, upon administration of octreotide, the headache is relieved or prophylactically prevented.

Another embodiment of the invention is a method of prophylactically treating headache in a subject, the method comprising administering to the subject at least once daily at least one dosage form comprising octreotide, to thereby treat the subject. In particular embodiments of the invention the headache is a vascular headache; in further embodiments of the invention the vascular headache is a migraine or a cluster headache; in a further embodiment of the invention the headache is caused by IIH; in a further embodiment of the invention the octreotide is administered orally; in a further embodiment of the invention the administering occurs at least 2 hours after a meal, or at least 1 hour before a meal.

Another embodiment of the invention is a method of aborting a headache in a subject, the method comprising orally administering to the subject at least once daily at least one dosage form comprising octreotide, to thereby treat the subject. In particular embodiments of the invention the headache is a vascular headache; in further embodiments of the invention the vascular headache is a migraine or a cluster headache; in a further embodiment of the invention the headache is caused by IIH; and in a further embodiment of the invention the administering occurs at least 2 hours after a meal or at least 1 hour before a meal.

The Oily Suspension

The oily suspension as used herein comprises an admixture of a hydrophobic medium (lipophilic fraction) and a solid form (hydrophilic fraction) wherein the solid form comprises a octreotide and at least one salt of a medium chain fatty acid, and wherein the medium chain fatty acid salt is present in the composition at an amount of 10% or more by weight or 11-20% or 11%, or 12% or 13% or 14% or 15% or 16% or 17%.

In further embodiments of the methods of the invention, the medium chain fatty acid salt in the solid form has a chain length from about 6 to about 14 carbon atoms; the medium chain fatty acid salt is sodium hexanoate, sodium heptanoate, sodium octanoate, sodium nonanoate, sodium decanoate, sodium undecanoate, sodium dodecanoate, sodium tridecanoate or sodium tetradecanoate, or a corresponding potassium or lithium or ammonium salt or a combination thereof, the fatty acid salt is sodium octanoate (sodium caprylate); the medium chain fatty acid salt is present in the oily suspension at an amount of 11% to 40% by weight, or at an amount of 12% to 18% by weight, preferably 15% by weight. In a specific embodiment the oily suspension comprises 15% w/w sodium octanoate. In another specific embodiment the oily suspension comprises 10-20% e.g. 15% w/w sodium decanoate. In another embodiment the solid form in the oily suspension additionally comprises a matrix forming polymer, which can be for example dextran or polyvinylpyrrolidone (PVP). In another embodiment the polyvinylpyrrolidone is present in the oily suspension at an amount of about 2% to about 20% by weight, or about 5% to about 15% by weight or about 10% by weight. In a specific embodiment the polyvinylpyrrolidone is PVP-12 and has a molecular weight of about 2500-3000. In another embodiment the hydrophobic medium comprises glyceryl tricaprylate and in a specific embodiment herein the oily suspension comprises 50-70% w/w glyceryl tricaprylate. In another embodiment the hydrophobic medium comprises a mineral oil, paraffin, a fatty acid such as octanoic acid, a monoglyceride, a diglyceride, a triglyceride, an ether or an ester, or a combination thereof. In another embodiment the triglyceride is a long chain triglyceride, a medium chain triglyceride or a short chain triglyceride. In another embodiment the triglyceride is a short chain triglyceride or a medium chain triglyceride or a mixture thereof. In another embodiment the short chain triglyceride is glyceryl tributyrate and the medium chain triglyceride is glyceryl tricaprylate. In another embodiment the hydrophobic medium further comprises an ionic surfactant or a non-ionic surfactant.

In further embodiments the surfactant is a monoglyceride, a cremophore, a polyethylene glycol fatty alcohol ether, a sorbitan fatty acid ester, a polyoxyethylene sorbitan fatty acid ester, Solutol HS15(polyoxyethylene esters of 12-hydroxystearic acid), or a poloxamer or a combination thereof. In further embodiments of the methods of the invention the monoglyceride is glyceryl monocaprylate, glyceryl monoocatnoate, glyceryl monodecanoate, glyceryl monolaurate, glyceryl monomyristate, glyceryl monopalmitate or glyceryl monooleate or glyceryl monostearate or a combination thereof. In further embodiments of the method, the polyoxyethylene sorbitan fatty acid ester is polyoxyethylene sorbitan monooleate (also termed polysorbate 80 or Tween 80).

In further embodiments the oily suspension comprises 3% w/w polyoxyethylene sorbitan monooleate. In further embodiments the hydrophobic medium additionally contains glyceryl monocaprylate and the oily suspension comprises 4% w/w glyceryl monocaprylate. In further embodiments the hydrophobic medium consists essentially of glyceryl tricaprylate and glyceryl monocaprylate. In further embodiments the hydrophobic medium comprises a triglyceride and a monoglyceride; in some embodiments the monoglyceride has the same fatty acid radical as the triglyceride; in some embodiments the triglyceride is glyceryl tricaprylate and the monoglyceride is glyceryl monocaprylate.

In some embodiments of the method the medium chain fatty acid salt in the water-soluble composition has the same fatty acid radical as the medium chain monoglyceride or the medium chain triglyceride or a combination thereof. In some embodiments of the method the medium chain fatty acid salt is sodium caprylate (sodium octanoate) and the monoglyceride is glyceryl monocaprylate and the triglyceride is glyceryl tricaprylate. In some embodiments of the method the oily suspension comprises magnesium chloride.

In one embodiment of the method, the oily suspension comprises about 3% octreotide, 5-15% PVP-12, 10-20% sodium caprylate (sodium octanoate), 2-10% surfactants, 50-70% lipid and stabilizer.

In a particular embodiment the formulation consists essentially of an oily suspension which comprises an admixture of a hydrophobic medium and a solid form wherein the solid form comprises a therapeutically effective amount of octreotide and about 10-20% preferably 15% medium chain fatty acid salt preferably sodium octanoate, and about 5-10% preferably 10% PVP-12; and wherein the hydrophobic medium comprises about 20-80%, preferably 30-70% triglyceride preferably glyceryl tricaprylate or glyceryl tributyrate or castor oil or a mixture thereof, about 3-10% surfactants, preferably about 6%, preferably glyceryl monocaprylate and Tween 80; in particular embodiments the octreotide is present at an amount of less than 33%, or less than 25%, or less than 10%, or less than 5% or less than 1%. The solid form may be a particle (e.g., consist essentially of particles, or consists of particles). The particle may be produced by lyophilization or by granulation. In a particular embodiment the solid form may be a particle and may be produced by lyophilization or by granulation.

In a further embodiment the formulation consists essentially of an oily suspension which comprises an admixture of a hydrophobic medium and a solid form wherein the solid form comprises a therapeutically effective amount of octreotide and about 10-20% preferably 15% medium chain fatty acid salt preferably sodium octanoate and about 5-10% preferably 10% PVP-12; and wherein the hydrophobic medium comprises about 20-80%, preferably 30-70% medium or short chain triglyceride preferably glyceryl tricaprylate or glyceryl tributyrate, about 0-50% preferably 0-30% castor oil, about 3-10% surfactants, preferably about 6%, preferably glyceryl monocaprylate and Tween 80; in particular embodiments the octreotide is present at an amount of less than 33%, or less than 25%, or less than 10%, or less than 5% or less than 1%.

Oral Dosage Form

In an embodiment, the oral octreotide is administered in a dosage form described herein. An exemplary oral dosage forms includes an enteric-coated oral dosage form comprising a composition comprising a suspension which comprises an admixture of a hydrophobic medium and a solid form wherein the solid form comprises a therapeutically effective amount of octreotide, at least one salt of a medium chain fatty acid and polyvinylpyrrolidone (PVP), wherein the polyvinylpyrrolidone is present in the composition at an amount of 3% or more by weight (e.g., about 3% to about 20% by weight or about 5% to about 15% by weight), and wherein the at least one salt of a medium chain fatty acid salt is present in the composition at an amount of at least 12% or more by weight (e.g., about 12% to 40% by weight or about 12% to 18% by weight). In an embodiment, the hydrophobic medium comprises glyceryl tricaprylate and the solid form consists of polyvinylpyrrolidone with a molecular weight of about 3000, and sodium octanoate. In an embodiment, the hydrophobic medium additionally comprises castor oil or glyceryl monocaprylate or a combination thereof and a surfactant. In an embodiment, the hydrophobic medium consists of glyceryl tricaprylate, glyceryl monocaprylate, and polyoxyethylene sorbitan monooleate.

In an embodiment, the solid form consists essentially of octreotide, polyvinylpyrrolidone with a molecular weight of about 3000, and sodium octanoate. In an embodiment, the composition comprises about 41% of glyceryl tricaprylate, about 27% castor oil, about 4% glyceryl monocaprylate, about 2% polyoxyethylene sorbitan monooleate, about 15% sodium octanoate, about 10% polyvinylpyrrolidone with a molecular weight of about 3000, and about 1-3.5% by weight octreotide e.g. 1.5% or 2% or 2.5% or 3% or 3.3% octreotide. In an embodiment, the composition comprises about 65% glyceryl tricaprylate, about 4% glyceryl monocaprylate, about 2% polyoxyethylene sorbitan monooleate, about 15% sodium octanoate, about 10% polyvinylpyrrolidone with a molecular weight of about 3000 and about 1-5.5% by weight octreotide e.g. 1.5% or 2% or 2.5% or 3% or 3.3% or 4% or 5% or 5.5% octreotide. In an embodiment, the composition comprises a therapeutically effective amount of octreotide, about 12-21% of sodium octanoate, about 5-10% of polyvinylpyrrolidone with a molecular weight of about 3000, about 20-80% of glyceryl tricaprylate, about 0-50% castor oil, and about 3-10% surfactant. In an embodiment, the composition comprises a therapeutically effective amount of octreotide, about 12-21% of sodium octanoate, about 5-10% of polyvinylpyrrolidone with a molecular weight of about 3000, about 20-80% of glyceryl tricaprylate, and about 3-10% surfactant.

In an embodiment, the octreotide is present at an amount of less than 33% (e.g., less than 25%, less than 10%, less than 5%, less than 1%). In an embodiment, the composition comprises about 15% of sodium octanoate, about 10% of polyvinylpyrrolidone with a molecular weight of about 3000, about 30-70% glyceryl tricaprylate and about 6% of surfactant. In an embodiment, the surfactant is glyceryl monocaprylate or polyoxyethylene sorbitan monooleate.

In an embodiment, the solid form comprises a particle or a plurality of particles. In an embodiment, the solid form further comprises a stabilizer.

In an embodiment, the polyvinylpyrrolidone has a molecular weight of about 3000.

In an embodiment, the medium chain fatty acid salt has a chain length from about 6 to about 14 carbon atoms. In an embodiment, the medium chain fatty acid salt is sodium hexanoate, sodium heptanoate, sodium octanoate, sodium nonanoate, sodium decanoate, sodium undecanoate, sodium dodecanoate, sodium tridecanoate or sodium tetradecanoate, or a corresponding potassium or lithium or ammonium salt or a combination thereof. In an embodiment, the medium chain fatty acid salt is sodium octanoate. In another embodiment, the medium chain fatty acid salt is sodium decanoate.

In an embodiment, the hydrophobic oily medium comprises a mineral oil, a paraffin, a fatty acid a monoglyceride, a diglyceride, a triglyceride, an ether or an ester, or a combination thereof. In an embodiment, the medium chain fatty acid salt is a lithium, potassium or ammonium salt. In an embodiment, the hydrophobic oily medium comprises glyceryl tricaprylate. In an embodiment, the composition further comprises a surfactant.

The compositions described herein can be administered to a subject i.e., a human or an animal, in order to treat the subject with a pharmacologically or therapeutically effective amount of a therapeutic agent (octreotide) described herein. The animal may be a mammal e.g., a mouse, rat, pig, dog horse, cow or sheep. As used herein the terms "pharmacologically effective amount" or "therapeutically effective amount" or "effective amount" means that amount of a drug or pharmaceutical agent (the therapeutic agent) that will elicit the biological or medical response of a tissue, system, animal or human that is being sought by a researcher or clinician and/or halts or reduces the progress of the condition being treated or which otherwise completely or partly cures or acts palliatively on the condition, or prevents development of the condition.

As used herein, the term "treatment" as for example in "method of treatment" or "treat" or "treating" refers to therapeutic treatment, wherein the object is to reduce or reverse or prevent the symptoms of a disease or disorder. In some embodiments, the compounds or compositions disclosed herein are administered prior to onset of the disease or disorder. In some embodiments, the compounds or compositions disclosed herein are during or subsequent to the onset of the disease or disorder.

The function and advantages of these and other embodiments will be more fully understood from the following example. This example is intended to be illustrative in nature and is not to be considered as limiting the scope of the systems and methods discussed herein.

Example

A novel oral octreotide formulation was tested for efficacy and safety in a phase III multicenter open-label dose-titration baseline-controlled study for acromegaly.

Methods: 155 complete or partially controlled patients were enrolled [IGF-I<1.3 upper limit of normal (ULN), and 2-hr integrated growth hormone (GH)<2.5 ng/mL] while receiving injectable somatostatin receptor ligand (SRL) for ≥3 months. Subjects were switched to 40 mg/day oral octreotide capsules (OOC), dose escalated to 60, and up to 80 mg/day, to control IGF-I. Subsequent fixed-doses were maintained for 7 month core treatment, followed by voluntary 6 month extension.

Results: Of 151 evaluable subjects initiating OOC, 65% maintained response and achieved the primary endpoint of IGF-I<1.3 ULN and mean integrated GH<2.5 ng/mL at the end of the core treatment period and 62% at the end of treatment (up to 13 months). The effect was durable and 85% of subjects initially controlled on OOC, maintained this response up to 13 months. When controlled on OOC, GH levels were reduced compared to baseline and acromegaly-related symptoms improved. Of 102 subjects completing core treatment, 86% elected to enroll into 6-month extension. 26 subjects considered treatment failures (IGF-I≥1.3 ULN), terminated early and 23 withdrew for adverse events, consistent with those known for octreotide or disease-related.

Conclusions: OOC, an oral therapeutic peptide achieves efficacy in controlling IGF-I and GH following switch from injectable SRLs, for up to 13 months, with a safety profile consistent with approved SRLs. OOC appears to be effective and safe as acromegaly monotherapy.

Oral octreotide capsules (OOC) were employed which facilitate intestinal octreotide absorption by a novel transient permeability enhancer (TPE) formulation (28). The capsule containing 20 mg non-modified octreotide acetate formulated with TPE enables transient and reversible paracellular tight junction passage of molecules <70 kDa. The size limitation and limited permeability duration ensures that luminal pathogens and endobacterial toxins, are excluded (28). Ingestion of OOC by healthy volunteers achieved circulating octreotide levels and exposure comparable to those observed after subcutaneous octreotide injection (29).

As a single 20 mg dose of OOC suppressed basal and GHRH-elicited GH levels in healthy volunteers (29), the drug was tested for efficacy and safety in a phase III, multicenter, open-label, dose-titration baseline-controlled study, in acromegaly. Objectives were to determine OOC effectiveness in maintaining baseline biochemical response for up to 13 months, in acromegaly patients in whom prior treatment with an injectable SRL had been effective i.e. to assess the proportion of subjects maintaining baseline response levels following a switch to OOC.

This open-label, maintenance of response, baseline controlled, withdrawal study was conducted to evaluate OOC safety and efficacy in patients with acromegaly shown to tolerate and respond to injectable SRLs. This IRB-approved multicenter international study continued from March 2012 to November 2013 in 37 sites for ~15 months and included screening, and baseline periods of ~2 months, core treatment period of ≥7 months, voluntary 6-month extension for patients who completed the core study, and a follow-up period of 2 weeks.

Patient Population

Subjects had confirmed biochemical and clinical evidence for active acromegaly and were required to receive a stable dose of parenteral SRLs for at least 3 months prior to screening. At screening, patients had to demonstrate complete or partial response to SRLs, defined as IGF-I<1.3× ULN for age and integrated GH response over 2 hours <2.5 ng/mL. Patients were excluded if they received GH antagonists (within <3 months) or dopamine agonists (within <2 months), received radiotherapy within 10 years, or underwent pituitary surgery within 6 months prior to screening.

Screening and Baseline Periods

Screening and baseline periods (median 42 days) enabled assessment of subject eligibility and for establishing baseline disease control (IGF-1 and GH measurements), while receiving parenteral SRL injections. The first OOC dose was administered ≥4-weeks after the last SRL injection. On average, the last SRL dose was given approximately 2 weeks following Screening visit and 2 weeks prior to Baseline visit.

Treatment Period

The OOC treatment period lasted ≥13 months and comprised a dose escalation (2-5 months) followed by a fixed dose period (8-11 months). The fixed dose period included the time periods up to the completion of the core and extension treatment phases (at 7 and 13 months respectively). Enrollment into the extension phase was voluntary. OOC was administered in the morning and evening (≥1 hour prior to a meal and >2 hours after a meal).

Dose-Escalation

First OOC dose (20 mg+20 mg) was dispensed ≥4 weeks [mean (SD) 33.3 (12.62), median (P25,P75) 31.0 (29.0,35.0) days] after last SRL injection. OOC dose escalations (to 40+20 mg and if required to 40+40 mg), occurred after 2 successive visits if IGF-I was inadequately controlled on a stable dose i.e. >20% increase over prior levels, or emergence of acromegaly symptoms. Visits occurred every 14 days for IGF-I measurements, and results used to guide dosing decisions at the subsequent visit. Integrated GH levels (measured 2-4 hours following OOC administration) were measured with every dose escalation. Subjects could revert to parenteral SRL therapy at any time, for either safety or efficacy, at the discretion of the site.

Fixed-Dose

Subjects entered into the fixed-dose period when IGF-I levels were normalized or returned to baseline levels, during ≥2 successive visits. Per protocol, adequately controlled subjects completing the core treatment period were offered the option to continue a 6-month extension. At each monthly visit during the core treatment and bi-monthly during the extension, IGF-I was measured and acromegaly symptoms assessed. Integrated GH levels were measured at the beginning and end of the fixed-dose period (core and extension). The optimally effective OOC dose achieved during dose escalation was continued for the duration of the fixed-dose period, for up to 13 months.

Endpoints and Statistical Analysis

The primary efficacy endpoint was descriptive and defined as the proportion of responders at the end of the core treatment, with an exact 95% CI in the modified intent-to-treat (mITT) population (i.e. all subjects who had ≥1 post-first-dose efficacy assessment). Response was defined, similarly to the inclusion criteria as IGF-I<1.3 ULN for age and integrated GH<2.5 ng/mL (utilizing Last Observation Carried Forward imputation (LOCF)). At the end of extension, the primary endpoint was the proportion of responders, of all subjects who entered the extension (extension-ITT), and for those who entered the extension as responders, with an exact 95% CI. When continuous measures were reasonably symmetric, mean values and SD were used, otherwise both mean and median values are presented.

Secondary and exploratory descriptive endpoints included the proportion of subjects who achieved categorical response levels at end of treatment, based on IGF-I and/or GH levels, and the proportion of subjects who maintained response i.e. who remained responders from the beginning of the fixed-dose to end of the treatment periods.

Acromegaly symptoms (headache, asthenia, perspiration, swelling of extremities and joint pain), were scored by severity at each visit: absent=0, mild=1, moderate=2, severe=3. The proportion of subjects with improvement, no change or worsening in overall scores, as well as those with 1, 2 or 3 active symptoms from baseline to end of treatment was calculated.

Assays

IGF-I and GH were measured centrally by IDS-iSYS IGF-I(30) (IS-3900, Immunodiagnostic Systems, Boldon, UK) and IDS-iSYS hGH(31) (IS-3700, Immunodiagnostic Systems) assays, at the Endocrine Laboratory, Universitat Munchen, Germany, and Solstas Lab (Greensboro, NC, USA). Recombinant standards (98/574 for GH and 02/254 for IGF-I) yielded inter-assay variability of 4-8.7% (IGF-I) and 1.1-3.4% (GH), and sensitivity 8.8 ng/mL (IGF-I) and 0.04 ng/mL (GH) (30,31). Integrated GH levels were calculated from the mean of 5 samples collected every 30±5 minutes for 2 hours beginning 2 hours following drug dosing (or at time zero at screening and baseline visits) (31). IGF-I measurements were assayed from a single sample (time zero) and compared to age-related reference ranges (30). Routine laboratory safety assessments were performed centrally, and all samplings were after ≥8-hour fasting.

During the fixed dose period 46 subjects at a subset of sites underwent pharmacokinetic (PK) evaluation.

Results

Baseline Characteristics

Enrolled subjects had been receiving long-acting SRL injections for 3 months to >20 years at all dose ranges. Of the 155 subjects enrolled, 95 had IGF-1≤1 ULN and GH<2.5 ng/mL at baseline, of whom 67 (430%) had GH<1 ng/mL. 42 subjects entered the study with 1<IGF-1<1.3 and GH<2.5 ng/mL. While eligible patients had to meet criteria of complete or partial response to injectable SRLs at screening to enter the study, only 88.70 of these subjects were responding to injectable SRLs at baseline and 17 patients (11%) had IGF-1≤1.3 ULN and/or GH≥2.5 ng/mL. (See Table 1). 81% of subjects had active acromegaly symptoms despite treatment on injectables.

TABLE 1

| Baseline Characteristics of All Subjects Enrolled [N = 155] | | | |
|---|---|---|---|
| Demographics [n (%)] | | Symptomatic & Biochemical Control | |
| Age | | Acromegaly symptoms [n (%)] | |
| Mean (SD) | 54.2 (11.54) | Headache | 64 (41.3) |
| Gender | | Perspiration | 65 (41.9) |
| Female gender | 88 (56.8) | Asthenia | 68 (43.9) |
| Disease Characteristics [n (%)] | | Swelling of extremities | 58 (37.4) |
| Duration of acromegaly | | Joint pain | 87 (56.1) |
| <10 years | 74 (47.7) | At least one symptom | 125 (80.6) |
| 10-<20 years | 53 (34.2) | At least two symptoms | 91 (61.3) |
| ≥20 years | 28 (18.1) | At least three symptoms | 67 (43.2) |
| Pituitary tumor characteristic | | IGF-I (ULN) | |
| Microadenoma | 51 (32.9) | Mean (SD) | 0.94 (0.250) |
| Intrasellar macroadenoma | 53 (34.2) | Median (P25, P75) | 0.89 (0.76, 1.07) |
| Extrasellar macroadenoma | 46 (29.7) | GH (mean ng/mL) | |
| Other | 5 (3.2) | Mean (SD) | 0.93 (0.716) |
| Medical Treatment [n (%)] | | Median (P25, P75) | 0.77 (0.44, 1.23) |
| Previous treatments for acromegaly | | Biochemical control [n (%)] | |
| Surgery | 121 (78.1) | IGF-I ≤1 ULN & GH <2.5 ng/mL | 95 (61) |
| Medication, other than SRLs | 61 (39.4) | IGF-1 ≤1 ULN and GH <1 ng/mL | 67 (43) |
| Radiation | 13 (8.4) | IGF-1 ≤1 ULN and 1 ≤ GH <2.5 ng/mL | 28 (18) |
| Surgery followed by radiation | 8 (5.2) | 1 < IGF-I <1.3 & GH <2.5 ng/mL | 42 (27) |
| Radiation followed by surgery | 1 (0.6) | IGF-I ≥1.3 and/or GH ≥2.5 ng/mL | 18 (12) |
| Previous SRLs treatment [n (%)] | | | |
| Octreotide LAR[1] (mg) | 97 (62.6) | | |
| 10, 20 | 64 (66% of pts on octreotide) | | |
| 30, 40, 60 | 33 (34% of pts on octreotide) | | |
| Lanreotide[2] (mg) | 58 (37.4) | | |
| 60, 90 | 27 (47% of pts on lanreotide) | | |

TABLE 1-continued

Baseline Characteristics of All Subjects Enrolled [N = 155]

| Demographics [n (%)] | | Symptomatic & Biochemical Control |
|---|---|---|
| 120 | 31 (53% of pts on lanreotide) | |
| Time receiving parenteral SRLs [n (%)] | | |
| <1 year | 21 (13.5) | |
| 1-<5 years | 63 (40.6) | |
| 5-<10 years | 37 (23.9) | |
| >=10 years | 34 (21.9) | |
| Subjects on Combo cabergoline/pegvisomant[3] [n (%)] | 18 (11.6) | |

[1]Sandostatin LAR,
[2]Somatuline Autogel
[3]Subjects on combination therapy with cabergoline/pegvisomant within the last 6 months prior to screening.

Subject Disposition 235 patients were screened and most of those failing to meet inclusion criteria had IGF-I≥1.3ULN. 155 subjects (67 males, 88 females) were enrolled, 151 underwent at least one biochemical assessment after first OOC dose, (mITT), 110 (71%) entered the fixed dose period, 88 elected to continue into the 6 months extension and 82 subjects completed 13 months treatment.

59 subjects discontinued treatment during the course of the study, most (n=45; 76%), during the dose-escalation period. Early terminations were due to treatment failure (IGF-I>1.3 ULN; n=26; 16.8%), adverse events (n=23; 14.8%), patient choice (n=7; 4.5%), lost to follow-up (n=2; 1.3%) and sponsor request (n=1; 0.6%).

Efficacy

Overall, 65% of all enrolled subjects (mITT population, N=151, 95% CI 58.4-74.2), were responders up to 7 months, and 62% were responders up to 13 months (95% CI 54.9-71.7), as compared to 88.7% at the baseline visit while on injectable SRLs. Sensitivity analysis (Markov Chain Monte Carlo multiple imputation), showed 65.6% response, consistent with primary LOCF analysis.

The effect was durable as 85% and 89% of subjects who entered the fixed dose and extension periods respectively as responders, maintained response for up to 13 months treatment. 78.4% [95% CI 68.4, 86.5] of subjects who entered the extension were responders at end of treatment (up to 13 months). At the beginning of the fixed dose phase 51/110 (46%) were treated on 40 mg, 25/110 (23%) on 60 mg and 34/110 (31%) on 80 mg. The response up to 13 months, for those patients that entered the fixed dose, was 88% (95% CI 76.1-95.6), 84% (95% CI 63.9-95.5) and 47% (95% CI 29.8-64.9), for 40 mg, 60 mg and 80 mg respectively.

Table 2 depicts biochemical response categories at baseline and end of treatment for all evaluable patients. Integrated GH levels <2.5 ng/mL were achieved in 93% of mITT subjects at the end of treatment versus 96% at baseline, while GH levels <1 ng/mL were achieved in 78% of subjects versus 66% at baseline. GH levels were decreased from 0.77 at baseline to 0.48 ng/mL at the end of treatment. While GH was maintained in 93% of subjects enrolled, 64% achieved IGF-I<1.3×ULN at the end of treatment versus 91% at baseline. 65 subjects (43% of mITT) entered the study with IGF-1≤1 ULN and GH<1 ng/mL, and 49 (32.5%) subjects exhibited this control at end of treatment.

TABLE 2

IGF-I and Mean Integrated GH Suppression at Baseline and End of Treatment

| | Baseline n (%) | End of Treatment n (%) |
|---|---|---|
| mITT population | N = 151 | N = 151 |
| IGF-I <1.3 ULN and GH <2.5 ng/mL | 134 (88.7) | 93 (61.6) |
| IGF-1 ≤1 ULN and GH <1 ng/mL | 65 (43.0) | 49 (32.5) |
| IGF-I ≥1.3 ULN AND/OR GH ≥2.5 ng/mL | 17 (11.3) | 58 (38.4) |
| IGF-I <1.3 ULN | 138 (91.4) | 97 (64.2) |
| IGF-I ≤1.0 ULN | 96 (63.6) | 57 (37.7) |
| GH <2.5 ng/mL | 145 (96.0) | 140 (92.7) |
| GH <1.0 ng/mL | 100 (66.2) | 117 (77.5) |
| Median IGF-1 levels (Q1-Q3) | 0.90 (0.76-1.07) | 1.120 (0.870-1.440) |
| Median GH levels (Q1-Q3) | 0.77 (0.44-1.23) | 0.488 (0.244-0.870) |

Table 2 shows IGF-I and GH categories at Baseline and end of treatment (core+extension), for all enrolled subjects, with at least one efficacy measure on post first OOC dose (mITT population). This analysis also includes the 59 subjects who terminated early during the course of the study. For this analysis the last concentrations of IGF-I and GH on treatment were carried forward. mITT, modified Intent to Treat; IGF-1, Insulin Growth Factor-1; GH, Growth Hormone; ULN-Upper Limit of Normal. Q1-Q3, interquartile range Table 3 depicts biochemical response categories at the beginning of the fixed dose and end of 13 months treatment for those 110 subjects stabilized on OOC, who entered the fixed dose phase. Of these subjects, 91 (83%) were responders at the beginning of the fixed dose phase and 82 (75%) were responders at the end of treatment (LOCF imputation). During the fixed dose phase, both GH and IGF1 responses were largely maintained.

TABLE 3

IGF-I and Mean Integrated GH Suppression at the Beginning of Fixed-dose Period and at the End of 13-Month Treatment.

| | Beginning of Fixed Dose n (%) | End of Treatment n (%) |
|---|---|---|
| Fixed dose population | N = 110 | N = 110 |
| IGF-I <1.3 ULN and GH <2.5 ng/mL | 91 (82.7) | 82 (74.5) |

TABLE 3-continued

IGF-I and Mean Integrated GH Suppression at the Beginning
of Fixed-dose Period and at the End of 13-Month Treatment.

| | Beginning of Fixed Dose n (%) | End of Treatment n (%) |
|---|---|---|
| IGF-I ≥1.3 ULN OR GH ≥2.5 ng/mL | 19 (17.3) | 28 (25.5) |
| IGF-I <1.3 ULN | 91 (82.7) | 84 (76.4) |
| IGF-I ≤1.0 ULN | 59 (53.6) | 52 (47.3) |
| GH <2.5 ng/mL | 109 (99.1) | 105 (95.5) |
| GH <1.0 ng/mL | 97 (88.2) | 90 (81.8) |
| Median IGF-1 levels (Q1-Q3) | 0.98 (0.79-1.19) | 1.04 (0.83-1.26) |
| Median GH levels (Q1-Q3) | 0.40 (0.23-0.66) | 0.43 (0.23-0.76) |

Table 3 shows IGF-I and GH categories at Baseline and end of treatment (core+extension), for all subjects controlled on OOC and entering the fixed dose phase. For this analysis the last on treatment concentrations of IGF-I and GH were carried forward. IGF-1, Insulin Growth Factor-1; GH, Growth Hormone; ULN, Upper Limit of Normal. Q1-Q3, interquartile range.

Exploratory analysis showed that the degree of baseline control on injectable SRLs predicted subsequent response to OOC. The combination of IGF-I≤1ULN/GH<2.5 ng/mL and low to mid doses of injectable SRLs (octreotide <30 mg or lanreotide <120 mg), at screening, yielded an OOC response rate of 84.5% (49 of 58 subjects).

FIGS. 1A-1D show that mean IGF-I levels were stably maintained between the beginning to the end of the fixed-dose period, up to 13 months in both the mITT and fixed dose population. The slight increase in mean values from baseline towards the end of the dose-escalation period in the mITT population reflects those subjects failing to be controlled on OOC and discontinuing the study early, all of whom were included in the mITT analysis. Median GH levels at Baseline (0.77 ng/mL), were attenuated within 2 hours of the first OOC dose to 0.40 ng/mL and remained suppressed by the end the extension (0.49 ng/mL). In the fixed dose population median GH levels were 0.77 at baseline, and 0.43 ng/mL at the end of treatment.

80% of subjects entering the fixed dose improved or maintained acromegaly symptoms (26% maintained, 54% improved). Proportion of subjects with at least 1, 2 or 3 acromegaly symptoms decreased from 79%, 63% and 45% respectively at baseline to 68%, 48% and 31% at end of treatment. Acromegaly symptoms improved as demonstrated by the decline from baseline (on injectables) to end of treatment (OOC), in the proportion of subjects with active acromegaly symptoms.

Compliance

Over 94% of subjects fully complied with study drug administration in both the core treatment period and the extension, based on capsule counts, daily diaries, and a general drug administration and food habits questionnaire.

Pharmacokinetics

In 46 subjects studied during the fixed dose phase, mean plasma octreotide concentrations increased dose-dependently (see FIG. 2), and mean plasma octreotide trough values (at time zero), were comparable for the 40 and 60 mg regimens, each of which represent a prior 20 mg overnight dose, with a higher mean trough for the 80 mg regimen, which represents a 40 mg prior overnight dose. Steady-state mean apparent elimination half-life (t½) ranged from 3.19±1.07 (mean±SD, on 40 mg) to 4.47±2.02 hrs (on 80 mg)

Safety

Of 155 subjects in the safety population, 138 (89%) experienced an AE. Ninety two percent of events were mild to moderate (see below). Most commonly reported organ systems included gastrointestinal, neurologic and musculoskeletal, consistent with the known octreotide safety profile (1,20). Common gastrointestinal AEs (occurring in ≥5%), were nausea, diarrhea, dyspepsia, abdominal pain and distention, flatulence and vomiting, which mostly occurred within the first two months of treatment, and mostly resolved with treatment continuation (median AE duration=13 days). Common neurologic AEs were headache and dizziness and in the musculoskeletal system, arthralgia and back pain. Infections related to the gastrointestinal system included a single case of viral gastroenteritis. Hypoglycemia or hyperglycemia were reported in 7 and 11 subjects respectively (4.5% and 7%), neither of which led to early discontinuation. Hepatobiliary disorders were reported in 18 (11.6%); with cholelithiasis in 12 (7.7%). Clinically meaningful alterations were not observed in laboratory safety parameters, vital signs, ECG or physical examinations. Forty seven percent of AEs occurred within the first 3 months of treatment and the incidence significantly decreased with time from the dose escalation to the fixed dose phase.

Twenty one subjects (13.5%) experienced 39 serious AEs. Two were considered possibly related to OOC-elevated hepatic transaminases and jaundice occurred in a subject with severe dehydration and a subject with suspected bile duct obstruction. Four malignancies were reported, none of which were considered study drug-related. Serious gastrointestinal infections were not reported.

Twenty-three patients discontinued because of an AE, 19 of which were study-drug related, mostly in the first 3 months of treatment; ten earlier terminations were due to gastrointestinal symptoms, including nausea, diarrhea and abdominal pain. Two deaths were reported, neither of which were considered OOC-related. (See below). Overall, OOC safety was consistent with the known octreotide safety profile and acromegaly disease burden, with no new emerging safety signals related to the novel formulation and route of administration.

Discussion

In healthy volunteers 20 mg oral OOA yielded systemic drug exposure (AUC) comparable to 0.1 mg SC dose of octreotide (29). We now show clinical utility and unique mode of action of TPE, whereby a therapeutic peptide is effectively and safely delivered orally.

OOC is shown to exhibit efficacy in controlling and maintaining IGF-I and integrated GH levels, for ≥13 months in biochemically controlled acromegaly subjects after switching from injectable SRLs. The primary efficacy endpoint was achieved by 65% of subjects at the end of the core treatment and by 62% at the end of 13 months, compared to 89% on injectable SRLs at baseline. The effect was durable and 85% of 91 subjects who entered the fixed-dose period as responders maintained this response for up to 13 months. These results are comparable to those reported for 41 acromegaly patients responding to injectable octreotide LAR (IGF-1≤1.2 and GH<2.5 ng/mL). 84% of these maintained baseline IGF-I/GH control at 6 months (32).

Predictors of the degree of OOC responsiveness included good baseline control on injectable SRLs, (IGF-I≤1ULN/GH<2.5 ng/mL), and low to mid doses of injectable SRLs. OOC also showed efficacy in maintaining clinical response; improved acromegaly symptom severity was noted in subjects who entered the fixed dose phase.

As activity and safety of octreotide are well characterized, the primary goal was to assess safety and efficacy of an oral octreotide formulation. Parenteral treatment, shown to be effective, was withdrawn and replaced with OOC. As long-term maintenance of response to parenteral octreotide therapy is well established (33) and octreotide tachyphylaxis does not occur in acromegaly, a baseline-control of SRL responders shown here reflects an appropriate study design. This design also anticipates clinical practice whereby patients eligible to receive OOC would be those responding to and tolerating parenteral SRLs and then switched to an oral formulation.

The enrolled patient population is representative of acromegaly patients suitable for OOC therapy. Despite being biochemically controlled by receiving SRL injections as the standard of care, 81% of subjects still exhibited persistent acromegaly symptoms at baseline. The duration of residual IGF-I suppression after long-acting SRL withdrawal is not known, but is not expected beyond 8-12 weeks from withdrawal in a patient with active disease (34). In fact, GH levels may revert between 4-6 weeks after octreotide LAR withdrawal (35). Accordingly, SRL was withdrawn 4 weeks prior to the first OOC test dose and clinical and biochemical response measured for ≥13 subsequent months. Several additional factors highlight disease activity of the enrolled subjects. Thirty-nine percent had IGF-I>1 ULN at baseline. Of the patients enrolled, 41% were being treated with the highest doses of parenteral octreotide and lanreotide for disease control.

Ninety patients (58%) required >40 mg OOC doses to maintain response. Furthermore, dose up-titration against rising IGF-I levels, as well as the observed sustained IGF-I normalization achieved with OOC over the 13-month duration of the study, allayed the concern of parenteral SRL carryover effect.

OOC doses selected for dose titration to enable optimal IGF-I control were based on PK modeling to achieve effective therapeutic exposure to octreotide (21,36). Distribution of the fixed dose population by OOC dose requirements were similar to the experience with injectable SRLs where higher doses are not usually required for adequate control (37,38). PK analyses demonstrated dose proportional exposure to oral octreotide. Octreotide levels measured prior to the morning dose are reflective of trough levels of the previous night dose, and were within the range shown to effectively inhibit GH secretion (21,36).

The results show that under fasting conditions, 0° C. suppressed GH levels in nearly all subjects. However, in contrast to GH inhibition, the proportion of subjects maintaining IGF-1<1.3 ULN was lower. This suggests that OOC bioavailability was not a cause of non-response. Hepatic IGF-I generation is log-linear with GH levels (39). Octreotide acts primarily on the pituitary to suppress GH secretion, but also directly inhibits hepatic IGF-I (24,25), and the observed mild discordant GH and IGF-I responses are commonly observed with SRL injections. The enhanced response of GH to OOC may also reflect that fasting GH levels were measured within 2-4 hours following the morning OOC dose, hence may not reflect trough levels. These results underscore that the somatotroph SSTR2 receptor is a primary target for the oral ligand and point to central control of GH hypersecretion by OOC, similar to the primary action of injectables.

The short GH half-life and the pulsatile nature of GH secretion (40,41) confound the accuracy of assessing GH levels based on a single blood test. The cutoff value of <2.5 ng/mL (integrated) for GH was chosen to distinguish excess from normal mortality in acromegaly. IGF-I<1.3 ULN was chosen because of the wide variances of IGF-I values and the challenge of reproducing a rigorous IGF-I<1 ULN even within individual patients (30,42).

OOC side effects are largely consistent with underlying acromegaly, as well as known to be associated with SRLs (16,20) only with no injection site reactions. Most adverse events occurred within the first 60 days and mostly resolved on treatment. Fluctuations in circulating octreotide levels (e.g. after withdrawal of injectable SRLs and followed by OOC initiation) are known to result in transient AEs (Sandostatin LAR label). Gastrointestinal symptoms, associated with octreotide, were also largely transient and reported early in the study and resolved on continued treatment. Adverse events were not dose-related. No route-of-administration-related safety signals or formulation-related AEs were encountered.

As OOC exhibits GH/IGF-I control, responders to parenteral SRL injection could be switched to 0° C. and avoid the burden of injections. Although compliance with food restrictions might be perceived as challenging for some, the advantages of an oral vs parenteral SRL preparation include convenience with ease of administration, precluding painful injections, and obviating monthly clinic visits and dependence on health care providers and/or family members for injection. Moreover, dose titration and symptomatic control could be achieved more efficiently with an oral SRL than with a 30-day preparation.

This novel TPE technology safely and successfully allowed oral delivery of a therapeutic peptide that achieved systemic endocrine effects. Twice daily OOC appears to offer a safe option for acromegaly monotherapy. See FIG. 4, which provides a flowchart of the study.

Pharmacokinetic Sampling

During the second monthly visit of the fixed dose phase, and after receiving the therapeutic regimen for at least 2 months, 46 subjects at a subset of sites underwent pharmacokinetic (PK) evaluation. Octreotide plasma concentrations were determined at 0 (pre-dose, up to 60 minutes before the morning drug administration),), and thereafter at 0.5, 1, 1.5, 2, 2.5, 3, 3.5, 4, 4.5, 5, 6, 8, and 12 hours post-dosing. Plasma concentrations of octreotide were measured using a validated LC/MS/MS method by PPD (Richmond, VA). The limit of quantitation (LOQ) for plasma octreotide concentrations was 0.0227 ng/mL.

Pharmacokinetics Analysis

Actual blood sampling times were used for pharmacokinetic (PK) analyses and per protocol times were used to calculate concentrations for graphical displays. Values below LLOQ up to the time at which the first quantifiable concentration or at last time were set to zero. Values below LLOQ that are embedded between two quantifiable values were set to missing. PK calculations were done using SAS®. PK parameters were derived from the plasma concentration actual time data, calculated using non compartmental analysis. Concentrations that were missing or not reportable were treated as missing values.

PK parameters $C_0$, $C_{max}$, $T_{max}$, and $T_{lag}$ were taken directly from the concentration time data. The elimination rate constant, $\lambda z$, was calculated as the negative of the slope of the terminal log-linear segment of the plasma concentration-time curve. The slope was determined from a linear regression of the natural logarithm of the terminal plasma concentrations against time; at least 3 terminal plasma concentration time points, beginning with the final concentration ≥LOQ, were selected for the determination of $\lambda z$ and the regression had to have a coefficient of determination ($r^2$)≥0.9000. The range of data used for each subject was determined by visual inspection of a semi-logarithmic plot of concentration vs. time. Elimination half-life (t½) was calculated according to the following equation:

$$t\frac{1}{2} = \frac{0.693}{\lambda z}$$

Area under the curve to the final sample with a concentration ≥LOQ [AUC(0-t)] was calculated using the linear trapezoidal method.

Safety

Two deaths were reported, neither of which were reported as study drug related. One was a 37-year-old male with a 10-year history of multiple surgeries for extrasellar pituitary macroadenoma. Six months after OOC initiation he had a suspected biliary obstruction, and subsequently also developed sepsis and multiple organ failure. At autopsy, no evidence for biliary obstruction was observed. The second was a 60-year-old male with cardiovascular risk factors, diagnosed with pancreatic cancer after six months into the study, and suffered a fatal myocardial infarction.

TABLE 4

Incidence of Most Common (≥5%) Adverse Events by System Organ Class and Preferred Term in all enrolled patients (n = 155), up to 13 months treatment.

| Adverse Event by System Organ Class and Preferred term | Number of subjects (%) |
|---|---|
| Gastrointestinal disorders | |
| Nausea | 46 (29.7) |
| Diarrhea | 31 (20) |
| Abdominal pain upper | 15 (9.7) |
| Dyspepsia | 14 (9) |
| Abdominal pain | 12 (7.7) |
| Flatulence | 10 (6.5) |
| Abdominal distension | 10 (6.5) |
| Vomiting | 10 (6.5) |
| Nervous system disorders | |
| Headache | 56 (36.1) |
| Dizziness | 9 (5.8) |
| Musculoskeletal and connective tissue disorder | |
| Arthralgia | 46 (29.7) |
| Back Pain | 9 (5.8) |
| General disorders and administration site conditions | |
| Asthenia | 38 (24.5) |
| Peripheral edema | 26 (16.8) |
| Fatigue | 8 (5.2) |
| Infections and infestations | |
| Nasopharyngitis | 12 (7.7) |
| Influenza | 11 (7.1) |
| Upper respiratory tract infection | 11 (7.1) |
| Skin and subcutaneous tissue disorders | |
| Hyperhidrosis | 36 (23.2) |
| Hepatobiliary disorders | |
| Cholelithiasis | 12 (7.7) |
| Vascular disorders | |
| Hypertension | 11 (7.1) |

REFERENCES

1. Melmed S. Medical progress: Acromegaly. N Engl J Med 2006; 355:2558-2573
2. Colao A, Ferone D, Marzullo P, Lombardi G. Systemic complications of acromegaly: epidemiology, pathogenesis, and management. Endocr Rev 2004; 25:102-152
3. Ribeiro-Oliveira A, Jr., Barkan A. The changing face of acromegaly—advances in diagnosis and treatment. Nat Rev Endocrinol 2012; 8:605-611
4. Holdaway I M, Bolland M J, Gamble G D. A meta-analysis of the effect of lowering serum levels of GH and IGF-I on mortality in acromegaly. Eur J Endocrinol 2008; 159:89-95
5. Sherlock M, Reulen R C, Aragon-Alonso A, Ayuk J, Clayton R N, Sheppard M C, Hawkins M M, Bates A S, Stewart P M. A paradigm shift in the monitoring of patients with acromegaly: last available growth hormone may overestimate risk. J Clin Endocrinol Metab 2014; 99:478-485
6. Burgers A M, Biermasz N R, Schoones J W, Pereira A M, Renehan A G, Zwahlen M, Egger M, Dekkers O M. Meta-analysis and dose-response metaregression: circulating insulin-like growth factor I (IGF-I) and mortality. J Clin Endocrinol Metab 2011; 96:2912-2920
7. Ayuk J, Clayton R N, Holder G, Sheppard M C, Stewart P M, Bates A S. Growth hormone and pituitary radiotherapy, but not serum insulin-like growth factor-I concentrations, predict excess mortality in patients with acromegaly. J Clin Endocrinol Metab 2004; 89:1613-1617
8. Dekkers O M, Biermasz N R, Pereira A M, Romijn J A, Vandenbroucke J P. Mortality in acromegaly: a metaanalysis. J Clin Endocrinol Metab 2008; 93:61-67
9. Jane J A, Jr., Starke R M, Elzoghby M A, Reames D L, Payne S C, Thorner M O, Marshall J C, Laws E R, Jr., Vance M L. Endoscopic transsphenoidal surgery for acromegaly: remission using modern criteria, complications, and predictors of outcome. J Clin Endocrinol Metab 2011; 96:2732-2740
10. Lee C C, Vance M L, Xu Z, Yen C P, Schlesinger D, Dodson B, Sheehan J. Stereotactic radiosurgery for acromegaly. J Clin Endocrinol Metab 2014; 99:1273-1281
11. van der Lely A J, Biller B M, Brue T, Buchfelder M, Ghigo E, Gomez R, Hey-Hadavi J, Lundgren F, Rajicic N, Strasburger C J, Webb S M, Koltowska-Haggstrom M. Long-term safety of pegvisomant in patients with acromegaly: comprehensive review of 1288 subjects in ACROSTUDY. J Clin Endocrinol Metab 2012; 97:1589-1597
12. Sherlock M, Woods C, Sheppard M C. Medical therapy in acromegaly. Nat Rev Endocrinol 2011; 7:291-300
13. Giustina A, Chanson P, Kleinberg D, Bronstein M D, Clemmons D R, Klibanski A, van der Lely A J, Strasburger C J, Lamberts S W, Ho K K, Casanueva F F, Melmed S. Expert consensus document: A consensus on the medical treatment of acromegaly. Nat Rev Endocrinol 2014; 10:243-248
14. Marko N F, LaSota E, Hamrahian A H, Weil R J. Comparative effectiveness review of treatment options for pituitary microadenomas in acromegaly. Journal of neurosurgery 2012; 117:522-538
15. Melmed S. Acromegaly pathogenesis and treatment. J Clin Invest 2009; 119:3189-3202
16. Lamberts S W, Uitterlinden P, Verschoor L, van Dongen K J, del Pozo E. Long-term treatment of acromegaly with the somatostatin analogue SMS 201-995. N Engl J Med 1985; 313:1576-1580.
17. Shimon I, Yan X, Taylor J E, Weiss M H, Culler M D, Melmed S. Somatostatin receptor (SSTR) subtype-selective analogues differentially suppress in vitro growth hormone and prolactin in human pituitary adenomas.

Novel potential therapy for functional pituitary tumors. J Clin Invest 1997; 100:2386-2392

18. Bauer W, Briner U, Doepfner W, Haller R, Huguenin R, Marbach P, Petcher T J, Pless. SMS 201-995: a very potent and selective octapeptide analogue of somatostatin with prolonged action. Life Sci 1982; 31:1133-1140

19. Lamberts S W, Oosterom R, Neufeld M, del Pozo E. The somatostatin analog SMS 201-995 induces long-acting inhibition of growth hormone secretion without rebound hypersecretion in acromegalic patients. J Clin Endocrinol Metab 1985; 60:1161-1165

20. Freda P U. Somatostatin analogs in acromegaly. J Clin Endocrinol Metab 2002; 87:3013-3018

21. Lancranjan I, Bruns C, Grass P, Jaquet P, Jervell J, Kendall-Taylor P, Lamberts S W, Marbach P, Orskov H, Pagani G, Sheppard M, Simionescu L. Sandostatin LAR: a promising therapeutic tool in the management of acromegalic patients. Metabolism 1996; 45:67-71

22. Ho K Y, Weissberger A J, Marbach P, Lazarus L. Therapeutic efficacy of the somatostatin analog SMS 201-995 (octreotide) in acromegaly. Effects of dose and frequency and long-term safety. Ann Intern Med 1990; 112:173-181

23. Chanson P, Borson-Chazot F, Kuhn J M, Blumberg J, Maisonobe P, Delemer B, Lanreotide Acromegaly Study G. Control of IGF-I levels with titrated dosing of lanreotide Autogel over 48 weeks in patients with acromegaly. Clin Endocrinol (Oxf) 2008; 69:299-305

24. Murray R D, Kim K, Ren S G, Chelly M, Umehara Y, Melmed S. Central and peripheral actions of somatostatin on the growth hormone-IGF-I axis. J Clin Invest 2004; 114:349-356

25. Pokrajac A, Frystyk J, Flyvbjerg A, Trainer P J. Pituitary-independent effect of octreotide on IGF-I generation. European journal of endocrinology/European Federation of Endocrine Societies 2009;

26. Maggio E T, Grasso P. Oral delivery of octreotide acetate in Intravail® improves uptake, half-life, and bioavailability over subcutaneous administration in male Swiss webster mice. Regul Pept 2011; 167:233-238

27. Williams G, Ball J A, Burrin J M, Joplin G F, Bloom S R. Effective and lasting growth-hormone suppression in active acromegaly with oral administration of somatostatin analogue SMS 201-995. Lancet 1986; 2:774-778

28. Tuvia S, Pelled D, Marom K, Salama P, Levin-Arama M, Karmeli I, Idelson G H, Landau I, Mamluk R. A Novel Suspension Formulation Enhances Intestinal Absorption of Macromolecules Via Transient and Reversible Transport Mechanisms. Pharm Res 2014;

29. Tuvia S, Atsmon J, Teichman S L, Katz S, Salama P, Pelled D, Landau I, Karmeli I, Bidlingmaier M, Strasburger C J, Kleinberg D L, Melmed S, Mamluk R. Oral octreotide absorption in human subjects: comparable pharmacokinetics to parenteral octreotide and effective growth hormone suppression. J Clin Endocrinol Metab 2012; 97:2362-2369

30. Bidlingmaier M, Friedrich N, Emeny R T, Spranger J, Wolthers O D, Roswall J, Koerner A, Obermayer-Pietsch B, Hubener C, Dahlgren J, Frystyk J, Pfeiffer A F, Doering A, Bielohuby M, Wallaschofski H, Arafat A M. Reference Intervals for Insulin-like Growth Factor-1 (IGF-1) From Birth to Senescence: Results From a Multicenter Study Using a New Automated Chemiluminescence IGF-1 Immunoassay Conforming to Recent International Recommendations. J Clin Endocrinol Metab 2014: jc20133059

31. Manolopoulou J, Alami Y, Petersenn S, Schopohl J, Wu Z, Strasburger C J, Bidlingmaier M. Automated 22-kD growth hormone-specific assay without interference from Pegvisomant. Clin Chem 2012; 58:1446-1456

32. Chieffo C, Cook D, Xiang Q, Frohman L A. Efficacy and safety of an octreotide implant in the treatment of patients with acromegaly. J Clin Endocrinol Metab 2013; 98:4047-4054

33. Cozzi R, Montini M, Attanasio R, Albizzi M, Lasio G, Lodrini S, Doneda P, Cortesi L, Pagani G. Primary treatment of acromegaly with octreotide LAR: a long-term (up to nine years) prospective study of its efficacy in the control of disease activity and tumor shrinkage. J Clin Endocrinol Metab 2006; 91:1397-1403

34. Stewart P M, Stewart S E, Clark P M, Sheppard M C. Clinical and biochemical response following withdrawal of a long-acting, depot injection form of octreotide (Sandostatin-LAR). Clin Endocrinol (Oxf) 1999; 50:295-299

35. Biermasz N R, van den Oever N C, Frolich M, Arias A M, Smit J W, Romijn J A, Roelfsema F. Sandostatin LAR in acromegaly: a 6-week injection interval suppresses G H secretion as effectively as a 4-week interval. Clin Endocrinol (Oxf) 2003; 58:288-295

36. Wass J A. Octreotide treatment of acromegaly. Horm Res 1990; 33 Suppl 1:1-5; discussion 6

37. Fleseriu M. Clinical efficacy and safety results for dose escalation of somatostatin receptor ligands in patients with acromegaly: a literature review. Pituitary 2011; 14:184-193

38. Turner H E, Thornton-Jones V A, Wass J A. Systematic dose-extension of octreotide LAR: the importance of individual tailoring of treatment in patients with acromegaly. Clin Endocrinol (Oxf) 2004; 61:224-231

39. Barkan A L, Beitins I Z, Kelch R P. Plasma insulin-like growth factor-I/somatomedin-C in acromegaly: correlation with the degree of growth hormone hypersecretion. J Clin Endocrinol Metab 1988; 67:69-73.

40. Giustina A, Veldhuis J D. Pathophysiology of the neuroregulation of growth hormone secretion in experimental animals and the human. Endocr Rev 1998; 19:717-797

41. Reutens A T, Hoffman D M, Leung K C, Ho K K. Evaluation and application of a highly sensitive assay for serum growth hormone (GH) in the study of adult GH deficiency. J Clin Endocrinol Metab 1995; 80:480-485

42. Clemmons D R. Consensus statement on the standardization and evaluation of growth hormone and insulin-like growth factor assays. Clin Chem 2011; 57:555-559

Having thus described several aspects of at least one embodiment, it is to be appreciated that various alterations, modifications, and improvements will readily occur to those skilled in the art. Such alterations, modifications, and improvements are intended to be part of this disclosure and are intended to be within the scope of the invention. Accordingly, the foregoing description and drawings are by way of example only, and the scope of the invention should be determined from proper construction of the appended claims, and their equivalents.

The invention claimed is:

1. A method of treating acromegaly in a subject in whom prior treatment with a somatostatin analog has been shown to be effective and tolerated, the method comprising orally administering to the subject at least one dosage form comprising octreotide in the morning and at least one dosage form comprising octreotide in the evening, wherein the subject is orally administered octreotide twice per day, and wherein the oral administration provides improved control of acromegaly symptoms compared to treatment with an injectable somatostatin analog.

2. The method of claim 1, wherein the dosage form comprises an oily suspension which is formulated into a capsule.

3. The method of claim 2, wherein the capsule is enterically coated.

4. The method of claim 1, wherein the amount of octreotide in each dosage form is 20 mg.

5. The method of claim 1, wherein the morning oral administration comprises one or two dosage forms and the evening oral administration comprises one or two dosage forms.

6. The method of claim 1, wherein the morning oral administration comprises one dosage form and the evening oral administration comprises one dosage form.

7. The method of claim 1, wherein the morning oral administration comprises two dosage forms and the evening oral administration comprises one dosage form.

8. The method of claim 1, wherein the morning oral administration comprises two dosage forms and the evening oral administration comprises two dosage forms.

9. The method of claim 6, wherein the total amount of octreotide orally administered per day is 40 mg.

10. The method of claim 7, wherein the total amount of octreotide orally administered per day is 60 mg.

11. The method of claim 8, wherein the total amount of octreotide orally administered per day is 80 mg.

12. The method of claim 9, wherein the morning oral administration comprises 20 mg of octreotide and the evening oral administration comprises 20 mg of octreotide.

13. The method of claim 10, wherein the morning oral administration comprises 40 mg of octreotide and the evening oral administration comprises 20 mg of octreotide.

14. The method of claim 11, wherein the morning oral administration comprises 40 mg of octreotide and the evening oral administration comprises 40 mg of octreotide.

15. The method of claim 1, wherein the method is for long-term maintenance therapy in acromegaly patients.

16. The method of claim 9, wherein if insulin-like growth factor 1 (IGF-1) level of the subject is normal and the subject's clinical signs and symptoms are controlled, or biochemical and symptomatic response level of the subject is maintained by the oral administration of 40 mg daily of octreotide, then the total amount of octreotide orally administered per day is continued at 40 mg.

17. The method of claim 9, wherein if IGF-1 level of the subject is not normal and the subject's clinical signs and symptoms are not controlled, or biochemical and symptomatic response level of the subject is not maintained by the oral administration of 40 mg daily of octreotide, then the total amount of octreotide orally administered per day is increased to 60 mg.

18. The method of claim 10, wherein if IGF-1 level of the subject is normal and the subject's clinical signs and symptoms are controlled, or biochemical and symptomatic response level of the subject is maintained by the oral administration of 60 mg daily of octreotide, then the total amount of octreotide orally administered per day is continued at 60 mg.

19. The method of claim 10, wherein if IGF-1 level of the subject is not normal and the subject's clinical signs and symptoms are not controlled, or biochemical and symptomatic response level of the subject is not maintained by the oral administration of 60 mg daily of octreotide, then the total amount of octreotide orally administered per day is increased to 80 mg.

20. The method of claim 1, wherein the oral administration controls the growth hormone (GH) level or the IGF-1 level or acromegaly symptoms of the subject.

21. The method of claim 1, wherein 40 mg, 60 mg, or 80 mg of octreotide is orally administered to the subject per day.

\* \* \* \* \*